United States Patent
Beazley et al.

(10) Patent No.: US 10,851,385 B2
(45) Date of Patent: *Dec. 1, 2020

(54) CORN PLANT EVENT MON87460 AND COMPOSITIONS AND METHODS FOR DETECTION THEREOF

(71) Applicant: Monsanto Technology LLC, St. Louis, MO (US)

(72) Inventors: Kim A. Beazley, St. Louis, MO (US); Paolo Castiglioni, St. Louis, MO (US); Mark A. Dizigan, St. Louis, MO (US); Rebecca A. Kelly, St. Louis, MO (US); John A. Korte, St. Louis, MO (US); Amanda Rock, St. Louis, MO (US); Christine Voyles, St. Louis, MO (US)

(73) Assignee: Monanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/550,761

(22) Filed: Aug. 26, 2019

(65) Prior Publication Data
US 2019/0376078 A1  Dec. 12, 2019

Related U.S. Application Data

(60) Continuation of application No. 16/138,596, filed on Sep. 21, 2018, now Pat. No. 10,428,345, which is a
(Continued)

(51) Int. Cl.
*C12N 15/82* (2006.01)
*C12Q 1/68* (2018.01)
(Continued)

(52) U.S. Cl.
CPC ..... *C12N 15/8273* (2013.01); *C12N 15/1034* (2013.01); *C12N 15/8261* (2013.01); *C12Q 1/6895* (2013.01); *Y02A 40/146* (2018.01)

(58) Field of Classification Search
None
See application file for complete search history.

(56) References Cited

U.S. PATENT DOCUMENTS

| 4,535,060 A | 8/1985 | Comai |
| 5,658,772 A | 8/1997 | Odell et al. |

(Continued)

FOREIGN PATENT DOCUMENTS

| CN | 1933723 A | 3/2007 |
| WO | 1997/042327 A2 | 11/1997 |

(Continued)

OTHER PUBLICATIONS

Castiglioni et al., "Bacterial RNA Chaperones Confer Abiotic Stress Tolerance in Plants and Improved Grain Yield in Maize Under Water-Limited Conditions", Plant Physiology, Jun. 8, 2008, pp. 446-455, and Supplemental Materials and Methods S1 obtained online at http://www.plantphysiol.org/cgi/data/147/2/446/DC1/1, vol. 147, American Society of Plant Biologists.

(Continued)

*Primary Examiner* — Ashley K Buran
(74) *Attorney, Agent, or Firm* — Thompson Coburn LLP; Charles P. Romano; Lawrence Lavin

(57) ABSTRACT

The present invention provides a transgenic corn event MON87460, and cells, seeds, and plants comprising DNA diagnostic for the corn event. The invention also provides compositions comprising nucleotide sequences that are diagnostic for MON87460 in a sample, methods for detecting the presence of MON87460 event polynucleotides in a sample, and probes and primers for use in detecting nucleotide sequences that are diagnostic for the presence of MON87460 in a sample. The present invention also provides
(Continued)

methods of breeding with MON87460 to produce water deficit tolerance corn plants.

11 Claims, 5 Drawing Sheets

Specification includes a Sequence Listing.

Related U.S. Application Data continuation of application No. 14/968,235, filed on Dec. 14, 2015, now Pat. No. 10,100,328, which is a continuation of application No. 13/866,651, filed on Apr. 19, 2013, now Pat. No. 9,228,197, which is a division of application No. 12/919,845, filed as application No. PCT/US2009/035288 on Feb. 26, 2009, now Pat. No. 8,450,561.

(60) Provisional application No. 61/032,568, filed on Feb. 29, 2008.

(51) Int. Cl.
    *C12N 15/10* (2006.01)
    *C12Q 1/6895* (2018.01)

(56) References Cited

U.S. PATENT DOCUMENTS

| | | | |
|---|---|---|---|
| 5,801,030 | A | 9/1998 | McVey et al. |
| 6,262,341 | B1 | 7/2001 | Baszczynski et al. |
| 6,825,400 | B2 | 11/2004 | Behr et al. |
| 7,078,590 | B2 | 7/2006 | Ohsumi et al. |
| 7,112,731 | B2 | 9/2006 | Hoffbeck |
| 7,410,800 | B2 | 8/2008 | Bensen et al. |
| 7,786,353 | B2 * | 8/2010 | Fernandes .......... C12N 15/8261 800/289 |
| 8,450,561 | B2 * | 5/2013 | Beazley ............... C12Q 1/6895 800/289 |
| 9,228,197 | B2 * | 1/2016 | Beazley ............. C12N 15/8273 |
| 10,100,328 | B2 * | 10/2018 | Beazley ............. C12N 15/1034 |
| 10,428,345 | B2 * | 10/2019 | Beazley ................ C12Q 1/6895 |
| 2005/0097640 | A1 | 5/2005 | Fernandes |
| 2007/0117128 | A1 | 5/2007 | Smith et al. |

FOREIGN PATENT DOCUMENTS

| | | |
|---|---|---|
| WO | 2003/080809 A2 | 10/2003 |
| WO | 04067736 A2 | 8/2004 |
| WO | 2004101741 A2 | 11/2004 |
| WO | 2005/014791 A2 | 2/2005 |
| WO | 2005033318 A2 | 4/2005 |
| WO | 06097784 A1 | 9/2006 |
| WO | 06097853 A1 | 9/2006 |
| WO | 2007/014275 A2 | 2/2007 |
| WO | 2008/021207 A2 | 2/2008 |
| WO | 2009/111263 A1 | 9/2009 |

OTHER PUBLICATIONS

Ding et al., "Gene probe and nucleic acid molecule hybridization", Animal Loemic Epidemiology, Dec. 31, 2007, pp. 20-23.
English Translation of Office Action for Analogous Chinese Patent Application No. 20098019620.6 dated Dec. 12, 2012, 7 pages.
Etchegaray et al., "CspA, CspB, and CspG, major cold shock proteins of *Escherichia coli* are induced at low temeperature under conditions that completely block protein synthesis", Journal of Bacteriology, Dec. 31, 1999, pp. 1827-1830, vol. 181, Issue 6.
GenBank Accession CQ052887.
GenBank Accession CQ067979.
GenBank Accession CQ095038.
GenBank Accession CQ133788.
GenBank Accession CQ172331.
GenBank Accession CQ201497.
GenBank Accession CQ217022.
GenBank Accession CQ255603.
GenBank Accession CQ292694.
GenBank Accession CQ329682.
Genbank: AC012073.9, published on Apr. 21, 2005.
Hsu-Yang Lin et al., "Detection of Genetically Modified Soybeans and Maize by the Polymerase Chain Reaction Method", Journal of Food and Drug Analysis, 2000, pp. 200-207, vol. 8, No. 3.
Intellectual Property Appellate Board Decision on Indian Patent Application No. 2407/DELNP/2006 for "Methods for Enhancing Stress Tolerance in Plants and Methods Thereof" in the name of Monsanto Technology LLC, Jul. 5, 2013, 17 pages.
Monsanto CSP Expression Summary, "Protein Expression for CspB, CspA in the 2006 Mystic Field Location", Dec. 4, 2009, 7 pages.
Monsanto CSP Performance Summary, ;"Summarization of Cold and Drought Tolerance Data Obtained in Transgenic Corn, Cotton and *Arabidopsis* with Csp Constructs", Dec. 4, 2009, 20 pages.
Phadtare et al, "The Nucleic Acid Melting Activity of *Escherichia coli* CspE Is Critical for Transcription Antitermination and Cold Acclimation of Cells", The Journal of Biological Chemistry, 2002, pp. 7239-7245, vol. 277, No. 9.
Phadtare et al, "Three Amino Acids in *Escherichia coli* CspE Surface-exposed Aromatic Patch Are Cricital for Nucleic Acid Melting Activity Leading to Transcription Antitermination and Cold Acclimation of Cells", The Journal of Biological Chemistry, 2002, pp. 46706-46711, vol. 277, No. 48.
Sidhu et al., "Glyphosate-Tolerant Corn: The Composition and Feeding Value of Grain from Glyphosate-Tolerant Corn is Equivalent to that of Conventional Corn ( *Zea mays* L.) ", Journal of Agriculture Food Chemical, 2000, pp. 2305-2312, vol. 48, No. 6.
Willimsky et al., "Characterization of cspB, a Bacillus Subtilis Inducible Cold Shock Gene Affecting Cell Viability at Low Temperatures", Journal of Bacteriology, 1992, pp. 6236-6335, vol. 174, No. 20.
Zhang et al., "Primer-probe design in quantitative analysis of gene expression using TaqMan technology", Clinical Education of General Practice, Nov. 30, 2007, pp. 469-471.

* cited by examiner

TRANSGENE AND GENOMIC DNA JUNCTION REGION OF MON87460 gaggtcctgtatggaatcgtgttcgtttatttcccggggccggggcaaaaaagacggcaatgg
attgttggacttgacatgtgcggtgcgtgggtccaacccggcctggcttttgggccagcgcggg
ccgacatagtgaggcccaaaatttaaaagcacagctgcaggcccacggaaccagtggttatga
aaacggaaacaagatagtaaattttacctccttaaattgccaccgtatccaatatccaatt
caggtaatctattcctataaagcaccaatttccgctcttttcatctatcgtctgtcatgcgctc
tgttcctctccatcgtgtatcgcagataaaggttacatgcatttccatgcatgtgatgggata
aaaacaagaaaaaggttgacatgcatttccatgcagataaaggttacatggatttccttgga
gaaagtataataagactaaatgctgaggcggaggagagagagagaggagatgtgggtagtaaac
ttttagtcatctttgacacaagatcaaagaagatttgtgaaattatgcattaaaatatcgaaga
gctaactactacacgaataagctaaatggtaggctgcaaaggtgattacagctagcagttgact
ctattattaaacttcctcttagggcaacagtagttggaaaggttttttggtgctgcccagatg
caaactaaaatccatgcatcctctctcaacctggaaggtgggcctaaaaagatgatctaccat
ccacggatccacctgtcagctcaagttattggtttaggaaacagggacctacgtggagatgtg
tgctggacgggcgggcctccacctgtcacgccgcaggcggaacggtgcgaacgacgcacgct
tttgctgtgcgcctgtgcgtctggcggtcagcgcgagcgtgactgcgttttcgtttgcgttaga
cgacgatcatcgctggaaatttggtattctctcacgttgaaggaaatggattggagggagtat
gtagataaattttcaaagcgttagacggctgtctttGAGGAGGATCGCGAGCCAGCGACGAGGC
CGGCCCTCCCTCCGCTTCCAAAGAAACGCCCCCATCGCCACTATATACATACCCCCCCTCTC
CTCCCATCCCCCAACCCTACCACCACCACCACCACCTCCACCTCCTCCCCCTCGCTGCC
GGACGACGAGCTCCTCCCCCCTCCCCCTCCGCCGCCGCCGCGCCGGTAACCACCCCGCCCCTCT
CCTCTTTCTTTCTCCGTTTTTTTTTCCGTCTCGGTCTCGATCTTTGGCCTTGGTAGTTTGGGT
GGGCGAGAGGCGGCTTCGTGCGCGCCCAGATCGGTGCGCGGGAGGGCGGGATCTCGCGGCTGG
GGCTCTCGCCGGCGTGGATCCGGCCCGGATCTCGCGGGGAATGGGGCTCTCGGATGTAGATCTG
CGATCCGCCGTTGTTGGGGGAGATGATGGGGGGTTTAAAATTTCCGCCATGCTAAACAAGATCA
GGAAGAGGGGAAAAGGGCACTATGGTTTATATTTTTATATATTTCTGCTGCTTCGTCAGGCTTA
GATGTGCTAGATCTTTCTTTCTTCTTTTTGTGGGTAGAATTTGAATCCCTCAGCATTGTTCATC
GGTAGTTTTTCTTTTCATGATTTGTGACAAATGCAGCCTCGTGCGGAGCTTTTTTGTAGGTAGA
CCATGGTAGAAGGTAAAGTAAAATGGTTCAACTCTGAAAAAGGTTTCGGATTCATCGAAGTAGA
AGGTCAAGACGATGTATTCGTTCATTTCTCTGCTATTCAAGGCGAAGGCTTCAAAACTTTAGAA
GAAGGCCAAGCTGTTTCTTTTGAAATCGTTGAAGGAAACCGCGGACCACAAGCTGCTAACGTTA
CTAAAGAAGCGTGAATTTAAATGGGCCCGGGGGATCCACTAGTTCTAGCTATATCATCAATTTA
TGTATTACACATAATATCGCACTCAGTCTTTCATCTACGGCAATGTACCAGCTGATATAATCAG
TTATTGAAATATTTCTGAATTTAAACTTGCATCAATAAATTTATGTTTTGCTTGGACTATAAT
ACCTGACTTGTTATTTTATCAATAAATATTTAAACTATATTTCTTTCAAGATATCATTCTTTAC
AAGTATACGTGTTTAAATTGAATACCATAAATTTTTATTTTTCAAATACATGTAAAATTATGAA
ATGGGAGTGGTGGCGACCGAGCTCAAGCACACTTCAATTCCTATAACGGACCAAATCGCAAAAA
TTATAATAACATATTATTTCATCCTGGATTAAAAGAAAGTCACCGGGGATTATTTTGTGACGCC
GATTACATACGGCGACAATAAAGACATTGGAAATCGTAGTACATATTGGAATACACTGATTATA
TTAATGATGAATACATACTTTAATATCCTTACGTAGGATCGATCCGAATTCGCGACACGCGGCC
GCTCTAGAACTAGTGGATCCCCCCCTTAATTAAGGGGCTGCAGGAATTCATAACTTCGTATAA

Figure 3A

```
TGTATGCTATACGAAGTTATAGCTTGGTCGAGTGGAAGCTAGCTTTCCGATCCTACCTGTCACT
TCATCAAAAGGACAGTAGAAAAGGAAGGTGGCACCTACAAATGCCATCATTGCGATAAAGGAAA
GGCTATCATTCAAGATGCCTCTGCCGACAGTGGTCCCAAAGATGGACCCCCACCCACGAGGAGC
ATCGTGGAAAAGAAGACGTTCCAACCACGTCTTCAAAGCAAGTGGATTGATGTGATACTTCCA
CTGACGTAAGGGATGACGCACAATCCCACTATCCTTCGCAAGACCCTTCCTCTATATAAGGAAG
TTCATTTCATTTGGAGAGGACACGCTGAAATCACCAGTCTCTCTCTACAAGATCGGGGATCTCT
AGCTAGACGATCGTTTCGCATGATTGAACAAGATGGATTGCACGCAGGTTCTCCGGCCGCTTGG
GTGGAGAGGCTATTCGGCTATGACTGGGCACAACAGACAATCGGCTGCTCTGATGCCGCCGTGT
TCCGGCTGTCAGCGCAGGGGCGCCCGGTTCTTTTTGTCAAGACCGACCTGTCCGGTGCCCTGAA
TGAACTGCAGGACGAGGCAGCGCGGCTATCGTGGCTGGCCACGACGGGCGTTCCTTGCGCAGCT
GTGCTCGACGTTGTCACTGAAGCGGGAAGGGACTGGCTGCTATTGGGCGAAGTGCCGGGGCAGG
ATCTCCTGTCATCTCACCTTGCTCCTGCCGAGAAAGTATCCATCATGGCTGATGCAATGCGGCG
GCTGCATACGCTTGATCCGGCTACCTGCCCATTCGACCACCAAGCGAAACATCGCATCGAGCGA
GCACGTACTCGGATGGAAGCCGGTCTTGTCGATCAGGATGATCTGGACGAAGAGCATCAGGGGC
TCGCGCCAGCCGAACTGTTCGCCAGGCTCAAGGCGCGCATGCCCGACGGCGAGGATCTCGTCGT
GACGCATGGCGATGCCTGCTTGCCGAATATCATGGTGGAAAATGGCCGCTTTTCTGGATTCATC
GACTGTGGCCGGCTGGGTGTGGCGGACCGCTATCAGGACATAGCGTTGGCTACCCGTGATATTG
CTGAAGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAGCGGGACTCTGGGGTTCG
ATCCCCAATTCCCGATCGTTCAAACATTTGGCAATAAAGTTTCTTAAGATTGAATCCTGTTGCC
GGTCTTGCGATGATTATCATATAATTTCTGTTGAATTACGTTAAGCATGTAATAATTAACATGT
AATGCATGACGTTATTTATGAGATGGGTTTTTATGATTAGAGTCCCGCAATTATACATTTAATA
CGCGATAGAAAACAAAATATAGCGCGCAAACTAGGATAAATTATCGCGCGGTGTCATCTATG
TTACTAGATCGGGGATCGGGCCACTCGACCAAGCTATAACTTCGTATAATGTATGCTATACGAA
GTTATCGCGCCAAATCGTGAAGTTTCTCATCTAAGCCCCCATTTGGACGTGAATGTAGACACGT
CGAAATAAAGATTTCCGAATTAGAATAATTTGTTTATTGCTTTCGCCTATAAATACGACGGATC
GTAATTTGTCGTTTTATCAAAATGTACTTTCATTTTATAATAACGCTGCGGACATCTACATTTT
TGAATTGAAAAAAATTGGTAATTACTCTTTCTTTTTCTCCATATTGACCATCATACTCATTGC
TGATCCATGTAGATTTCacgttgaagaaaaatggatggagggaggaagtagataaagttttttg
ttgtatattgtgattttaatttgaaatcaagcttggtcaaaccgtggccgaaatttggcctggc
cactaatggccatgaaccaagcgtagtttgccgattacccgtcccgacggtacgactttctct
aatcgctcggttactgtcctgcaacctgcatctcatgactccaggccggccaacaccagcag
cgaccgcgaccaggctcctcctcctcctccagccacgggcaagaggccgcgcgcatgctctcgc
tcctgttccggtaatccggcccagtaccttggtaccgcaccgtacctgtaatctctatctcta
gttctctagtacatattaagtcaatagtgtagactgtaacactaccatgacttcatcctccctt
acctcgctctctgcgcacgcacaaaccaccttccgcccatataggagccgatatcgtgcccc
ccgtcctggccgcacgcttccctaaccctcgtggactaggcttccctccacgacgaggccac
gacaatggttgccccgcacgacgaggccgcggtgtgggcgaaggaggcgacgtgacctacagt
ccaaggcctcacatccacatacatgcgtcatctaattgattaatctatagcctggtcgcgctgt
gctgctactgcttgatcgacgagtgctgttgcgacccgtctgtcatcttcgtcagctagacgaa
gcatccgagtacaactctaaacatacgaacattttaataacgagagcatataacgataaatagt
gcttctacattaatgtatgttatcaatacttattgactcagtgacaaagcacggacatacatct
agtagttaataataaaataaataattaccttattaaacgatcatttattatataaatgtattt
attttttatgtacatataataagttattacaatctgacaatatatataagtgatagaacataaa
gtagaggaacaaacggaacgtaaaggaaaacgaagctagtcaggtagatgctcccgaggacaaa
```

Figure 3B

```
aaaaaagggcatagttgtcaagtttaatcttcccaagttttatcttacgtagtagtagagcga
gagcggtccaattaagggcacgcacagttgcagcaggtgcagggctccagtagccgcggcgggt
acgctcgcagtcgcagggcgccgcgcctagttctgctgcccggcccgggtcatgaaccaac
```

Figure 3C

CORN PLANT EVENT MON87460 AND COMPOSITIONS AND METHODS FOR DETECTION THEREOF

CROSS-REFERENCE TO RELATED APPLICATIONS

This application is a continuation of U.S. application Ser. No. 16/138,596, filed Sep. 21, 2018 which is a continuation of U.S. application Ser. No. 14/968,235, filed Dec. 14, 2015, now U.S. Pat. No. 10,100,328, which is a continuation of U.S. application Ser. No. 13/866,651, filed Apr. 19, 2013, now U.S. Pat. No. 9,228,197, which is a divisional application of U.S. application Ser. No. 12/919,845, filed Aug. 27, 2010, now U.S. Pat. No. 8,450,561, which was the National Stage of International Patent Application No. PCT/US2009/035288, filed Feb. 26, 2009, and incorporated by reference herein in its entirety, which claims benefit of U.S. Provisional Application Ser. No. 61/032,568 filed Feb. 29, 2008, which is incorporated by reference herein in its entirety.

INCORPORATION OF SEQUENCE LISTING

The sequence listing that is contained in the file named "54813_0003US.txt", which is 19,761 bytes (measured in operating system MS-Windows), created on Dec. 14, 2015, is filed herewith by electronic submission and incorporated herein by reference in its entirety.

FIELD OF THE INVENTION

Disclosed herein are transgenic cells, seeds, and plants which include recombinant DNA expressing a cold shock protein that imparts improved stress tolerance and/or yield to plants. The disclosure also includes methods of making, using and detecting such cells, seeds and plants. In particular, the present invention relates to stress tolerant corn plants designated as MON87460, and methods and compositions for detecting the presence of MON87460 DNA in a sample.

BACKGROUND OF THE INVENTION

Transgenic plants with improved agronomic traits such as yield, environmental stress tolerance, pest resistance, herbicide tolerance, improved seed compositions, and the like are desired by both farmers and seed producers. Although considerable efforts in plant breeding have provided significant gains in desired traits, the ability to introduce specific DNA into plant genomes provides further opportunities for generation of plants with improved and/or unique traits.

SUMMARY OF THE INVENTION

Compositions and methods related to transgenic water deficit stress tolerant corn plants designated MON87460, and progeny and populations thereof are provided herein.

In one aspect, this invention provides the transgenic corn plants designated MON87460 and seed of said plant as deposited with a shipment mailed on Jan. 31, 2008 with American Type Culture Collection (ATCC) and assigned Accession No. PTA-8910. Another aspect of the invention comprises progeny plants, or seeds, or regenerable parts of the plants and seeds of the plant MON87460. Progeny plants, or seeds, or regenerable parts of the plants and seeds comprising SEQ ID NO:1, SEQ ID NO:2, SEQ ID NO: 3, SEQ ID NO: 4, SEQ ID NO:7, or SEQ ID NO:24 are also provided herein.

Another aspect of the invention provides polynucleotides comprising a transgene/genomic junction region from corn plant MON87460. Polynucleotides are provided that comprise at least one transgene/genomic junction nucleic acid molecule selected from the group consisting of SEQ ID NO:1 through SEQ ID NO:4, SEQ ID NO:25, and complements thereof, wherein the junction molecule spans the transgene insertion site. A corn seed and plant material thereof comprising any one of SEQ ID NO:1 through SEQ ID NO:4 or SEQ ID NO:25, is an aspect of this invention.

The present invention is also directed to a nucleus of a corn cell of event MON87460, wherein said nucleus comprises a chromosome having a heterologous polynucleotide insert that provides for improved water deficit tolerance, wherein said heterologous polynucleotide comprises any one of SEQ ID NO:1 through SEQ ID NO:4. Of particular interest is a chromosome wherein the heterologous polynucleotide comprises a truncated rice actin promoter for expression of a cspB gene, and wherein said truncated rice actin promoter is adjacent to corn genomic sequence of SEQ ID NO:5. In certain embodiments, a corn chromosome comprising SEQ ID NO:1 and a heterologous transgenic insert comprising a truncated rice actin promoter that is operably linked to a cspB gene is provided. A 5' terminus of the heterologous transgenic insert can overlap a 3' terminus of SEQ ID NO:1 in certain embodiments. In certain embodiments, the corn chromosome can comprise SEQ ID NO:7 or SEQ ID NO:24. In certain embodiments, a chromosome of the invention is located within a corn cell that also contains a second unlinked heterologous polynucleotide for expression of a glyphosate resistant 5-enolpyruvylshikimate-3-phosphate synthase (CP4 EPSPS) protein. Plants or seed comprising any of the corn chromosomes of the invention are also provided. Also provided are a processed food or feed commodity prepared from a corn seed having a chromosome comprising SEQ ID NO:1 and a heterologous transgenic insert comprising a truncated rice actin promoter that is operably linked to a cspB gene, where the processed food or feed commodity comprises a detectable amount of a polynucleotide comprising a nucleotide sequence of SEQ ID NO: 1, SEQ ID NO:2, or a complement thereof. In certain embodiments, the food or the feed commodity comprises corn meal, corn flour, corn gluten, corn oil and corn starch. In certain embodiments, the polynucleotide can comprise a nucleotide sequence of SEQ ID NO: 3, SEQ ID NO: 4, or a complement thereof. In other embodiments, the polynucleotide can further comprise a nucleotide sequence contained in SEQ ID NO:5, SEQ ID NO:6, SEQ ID NO:7, or SEQ ID NO:24.

According to another aspect of the invention, a pair of nucleotide primers are used in a DNA detection method, wherein the primer pair when used in a nucleic acid amplification method produces an amplicon that contains any one of SEQ ID NO:1 through SEQ ID NO:4. Detection of any one of SEQ ID NO:1 through SEQ ID NO:4 in an amplicon produced in this manner is diagnostic for the presence of nucleic acids from corn plant MON87460 in the sample analyzed in the detection method. Such methods comprise: (a) contacting the sample comprising MON87460 genomic DNA with a DNA primer pair; and (b) performing a nucleic acid amplification reaction, thereby producing an amplicon; and (c) detecting the amplicon, wherein the amplicon comprises SEQ ID NO:1 through SEQ ID NO:4.

According to another aspect of the invention, methods of detecting the presence of DNA corresponding specifically to the corn plant MON87460 DNA in a sample are provided. Such methods comprising: (a) contacting the sample comprising MON87460 DNA with a DNA probe comprising any one of SEQ ID NO:1 through SEQ ID NO:4, or DNA molecules substantially homologous to SEQ ID NO:1 through SEQ ID NO:4 that hybridize under stringent hybridization conditions with genomic DNA from corn plant MON87460 and do not hybridize under stringent hybridization conditions with non-MON87460 corn plant DNA; (b) subjecting the sample and probe to stringent hybridization conditions; and (c) detecting hybridization of the probe to the corn plant MON87460 DNA.

According to another aspect of the invention, methods of producing water deficit stress tolerant corn plants are provided and comprise the step of crossing a first parental homozygous corn plant of event MON87460 with a second parental homozygous corn plant that lacks the water deficit stress tolerance trait, thereby producing water deficit stress tolerant hybrid progeny plants. In certain embodiments, a method of producing a drought tolerant corn plant comprising crossing a drought tolerant first parent corn plant comprising a SEQ ID NO:1 and a heterologous transgenic insert comprising a truncated rice actin promoter that is operably linked to a cspB gene, and a second parent corn plant, thereby producing a plurality of drought tolerant progeny plants is provided. In other embodiments, the insert can comprise SEQ ID NO:7 or SEQ ID NO:24.

Another aspect of the invention is a method of determining the zygosity of the progeny of corn event MON87460 using DNA amplification reactions and two primer sets. A first primer set is used for amplification of MON87460 corn DNA and a second primer set is used for amplification of native corn sequence encompassing the transgene insertion site in MON87460 genomic DNA. Where the template for amplification is a corn plant homozygous for the MON87460 DNA an amplicon is produced only from the first primer set. Where the template for amplification is a corn plant heterozygous for the MON87460 DNA, amplicons are produced only from both the first primer set and the second primer set.

Also encompassed by the present invention is hybrid corn seed comprising in its genome any one of SEQ ID NO:1 through SEQ ID NO:4 wherein at least one parent in the cross used to create said hybrid seed is MON87460.

Other specific embodiments of the invention are disclosed in the following detailed description.

BRIEF DESCRIPTION OF THE DRAWINGS

FIG. 3A, B, C provides sequence (SEQ ID NO:24) of the transgene and genomic DNA junction region of MON87460. Corn genomic flanking DNA sequence is shown in small letters. Transgene sequence inserted from pMON73608 is shown in capital letters.

DETAILED DESCRIPTION OF THE INVENTION

A transgenic corn plant, herein referred to as "MON87460", or "CspB-Zm Event MON87460" is tolerant to water deficit stress as the result of expression of a cspB protein from *E. coli* in cells of said transgenic plant. Use of the water deficit stress tolerant corn will provide major benefits to corn growers, for example providing 5-10% higher crop yields in western dryland acres where the average yearly rainfall is insufficient to support an agriculturally effective yield from wild-type corn plants. Additionally, MON87460 corn plants provide the benefit of drought insurance in central, eastern & southern corn belt by providing higher crop yields under drought conditions as compared to wild-type corn plants. Corn growers will also benefit from irrigation cost savings in regions where corn is typically grown under irrigation.

As used herein, "water deficit" means a period when water available to a plant is not replenished at the rate at which it is consumed by the plant. A long period of water deficit is colloquially called drought which can result in loss of a crop, even a crop enabled with the chromosomes of this invention. Lack of rain or irrigation may not produce immediate water stress if there is an available reservoir of ground water for the growth rate of plants. Plants grown in soil with ample groundwater can survive days without rain or irrigation without adverse affects on yield. Plants grown in dry soil are likely to suffer adverse affects with minimal periods of water deficit. Severe water stress can cause wilt and plant death; moderate drought can cause reduced yield, stunted growth or retarded development. Plants can recover from some periods of water stress without significantly affecting yield. However, water stress at the time of pollination can have an irreversible effect in lowering yield. Thus, a useful period in the life cycle of corn for observing water stress tolerance is the late vegetative stage of growth before tasseling. The testing of water stress tolerance is often done through the comparison to control plants. For instance, plants of this invention can survive water deficit with a higher yield than control plants. In the laboratory and in field trials drought can be simulated by giving plants of this invention and control plants less water than an optimally-watered control plant and measuring differences in traits.

Figure 1:
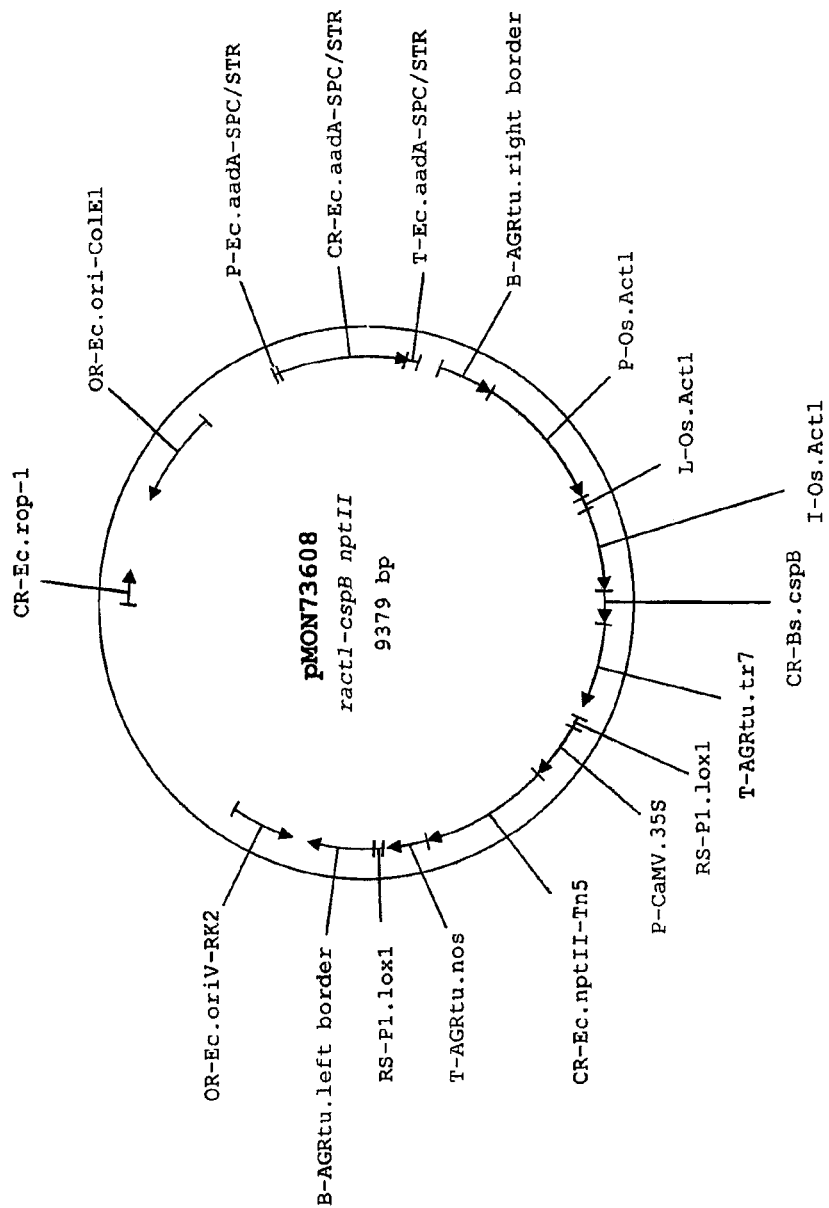
FIG. 1 provides a plasmid map of pMON73608.

The corn plant MON87460 was produced by *Agrobacterium* mediated transformation of an inbred corn line with the vector pMON73608 (FIG. 1). This vector contains the cspB coding region regulated by the rice actin promoter, the rice actin intron, and the tr7 3' polyadenylation sequence, and an nptII coding region regulated by the CaMV 35S promoter, and the NOS 3' polyadenylation sequence. Events generated from the vector pMON73608 were characterized by detailed molecular analyses.

A transgenic event in a plant occurs when recombinant DNA is inserted into a location in a chromosome in the nucleus. It is statistically improbable that any two separate transgenic events would be the same. Plants reproduced from a specific event will generally have consistency in trait. Not all transgenic events will provide transgenic plant seed, plants, or nuclei of this invention because of a variety of factors such as the location, copy number and integrity of the recombinant DNA in the chromosome, unintended insertion of other DNA, etc. As a result a desired transgenic event is identified by screening the transformed plant or its progeny seed for enhanced water deficit tolerance.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of plants in order to identify a plant characterized by optimal expression of an introduced gene of interest. For example, it has been observed in plants and in other organisms that there may be a wide variation in levels of expression of an introduced transgene among plants. There may also be differences in spatial or temporal patterns of expression, for example, differences in the relative expression of a transgene in various plant tissues, that may not correspond to the patterns expected from transcriptional regulatory elements present in the introduced gene construct. A plant that has desired levels or patterns of transgene expression is useful for introgressing the transgene into other genetic backgrounds by sexual crossing using conventional breeding methods. Progeny of such crosses maintain the transgene expression characteristics of the original transformant. This strategy is used to ensure reliable gene expression in a number of varieties that are well adapted to local growing conditions and market demands.

Events generated by transformation with pMON73608 were screened for insert number (number of integration sites within the corn genome), copy number (the number of copies of the T-DNA within one locus), the integrity of the inserted cassettes and the absence of backbone sequence using Southern blot analyses. Probes included the intact cspB and nptII coding regions and their respective promoters, introns, and polyadenylation sequences and the vector plasmid backbone. From approximately 140 initial transformants, events were selected based on copy number and backbone analysis for phenotypic analysis to identify plants having an improved phenotype from expression of cspB. Results of a greenhouse based test for water-deficit tolerance, identified a number of independent transformants having water deficit tolerance. Field testing of 22 selected transformants for water deficit tolerance under field growth conditions resulted in the identification of 10 improved events that were further tested for water-deficit tolerance and yield improvement and stability. Results of these further analyses identified MON87460 as having superior improved phenotypes. Extensive molecular characterization of MON87460 demonstrated that the event contains a single T-DNA insertion with one copy of both the cspB and nptII cassettes. Northern blot analysis confirmed that the expected size transcripts for both cspB and nptII are generated in MON87460. The data also surprisingly demonstrate that the *Agrobacterium* right border fragment is not present in MON87460 and that a truncation of the rice actin promoter regulating expression of the cspB gene has occurred such that only 108 bp (of 844 bp present in pMON73608) of the promoter DNA is present.

PCR and DNA sequence analyses were performed to determine the 5' and 3' insert-to-plant genome junctions, confirm the organization of the elements within the insert (FIG. 2), and determine the complete DNA sequence of the insert in corn plant MON87460 (SEQ ID NO:5). Analyses confirmed that the in planta T-DNA in MON87460 is identical to corresponding sequence from pMON73608, Sequence analysis also identified 1060 bp of 5' and 1260 bp of 3' flanking sequence for the MON87460 insert. Comparison to the sequence of wild-type DNA of the inbred line used for transformation showed that a 22 bp deletion of corn genomic DNA occurred at the site of integration of the MON87460 T-DNA.

It is advantageous to be able to detect the presence of transgene/genomic DNA of MON87460 in order to determine whether progeny of a sexual cross contain the transgene/genomic DNA of interest. In addition, a method for detecting MON87460 is useful when complying with regulations requiring the pre-market approval and labeling of foods derived from the recombinant crop plants. It is possible to detect the presence of a transgene by any well-known nucleic acid detection methods such as the polymerase chain reaction (PCR) or DNA hybridization using polynucleotide probes. These detection methods generally use DNA primer and probe molecules that are specific to the genetic elements, such as promoters, leaders, introns, coding regions, 3' transcription terminators, marker genes, etc, that are the components of the transgenes of a DNA construct. Such methods may not be useful for discriminating between different transgenic events, particularly those produced using the same transgene DNA construct unless the sequence of genomic DNA adjacent to the inserted transgene DNA is known. The present invention provides sequences and assays for detection of the novel transgene/genomic DNA border junctions of MON87460.

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Furthermore, disclosure herein of a given nucleic acid sequence necessarily defines its complementary sequence, as is known to one of ordinary skill in the art. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. Definitions of common terms in molecular biology may be found in Rieger et al., *Glossary of Genetics: Classical and Molecular*, 5th edition, Springer-Verlag: New York, 1991; and Lewin, *Genes V*, Oxford University Press: New York, 1994.

As used herein, the term "corn" means *Zea mays* and includes all plant varieties that can be bred with corn plant MON87460.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. Transgenic progeny having the same nucleus with either heterozygous or homozygous chromosomes for the recombinant DNA are said to represent the same transgenic event. Once a transgene for a trait has been introduced into a plant, that gene can be introduced into any plant sexually compatible with the first plant by crossing, without the need for directly transforming the second plant. The heterologous DNA and flanking genomic sequence adjacent to the inserted DNA will be transferred to progeny when the event is used in a breeding program and the enhanced trait resulting from incorporation of the heterologous DNA into the plant genome will be maintained in progeny that receive the heterologous DNA.

The term "event" also refers to the presence of DNA from the original transformant, comprising the inserted DNA and flanking genomic sequence immediately adjacent to the inserted DNA, in a progeny that receives inserted DNA including the transgene of interest as the result of a sexual cross of one parental line that includes the inserted DNA (e.g., the original transformant and progeny resulting from selfing) and a parental line that does not contain the inserted DNA. The term "progeny" denotes the offspring of any generation of a parent plant prepared in accordance with the present invention. A transgenic "event" may thus be of any generation. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location.

The present invention relates to the event MON87460 DNA, plant cells, tissues, seeds and processed products derived from MON87460. MON87460 corn plants may be self-pollinated to produce inbred lines that are homozygous for the MON87460 polynucleotides. The homozygous seed may be grown to produce homozygous progeny MON87460 event corn plants useful for crossing with other inbred corn plants to produce heterozygous hybrid corn seed. MON87460 hybrid corn seed can be grown to hybrid corn plants that exhibit water deficit tolerance and enhanced yield under stress conditions as compared to control plants.

Products that may be derived from MON87460 include foodstuffs and commodities produced from corn event MON87460. Such foodstuffs and commodities are expected to contain polynucleotides that, if detected in sufficient levels are diagnostic for the presence of corn event MON87460 materials within such commodities and foodstuffs. Examples of such foodstuffs and commodities include but are not limited to corn oil, corn meal, corn flour, corn gluten, corn cakes, corn starch, and any other foodstuff intended for consumption as a food source by an animal or otherwise, intended as a bulking agent, or intended as a component in a makeup composition for cosmetic use, etc.

It is also to be understood that two different transgenic plants can be mated to produce offspring that contain two independently segregating added, exogenous genes. Selfing of appropriate progeny can produce plants that are homozygous for both added, exogenous genes. Alternatively, inbred lines containing the individual exogenous genes may be crossed to produce hybrid seed that is heterozygous for each gene, and useful for production of hybrid corn plants that exhibit multiple beneficial phenotypes as the result of expression of each of the exogenous genes. Descriptions of breeding methods that are commonly used for different traits and crops can be found in various references, e.g., Allard, "Principles of Plant Breeding," John Wiley & Sons, NY, U. of CA, Davis, Calif., 50-98, 1960; Simmonds, "Principles of Crop Improvement," Longman, Inc., NY, 369-399, 1979; Sneep and Hendriksen, "Plant Breeding Perspectives," Wageningen (ed), Center for Agricultural Publishing and Documentation, 1979. Of particular interest in the present invention is the development of MON87460 event corn plants that express cspB protein and a glyphosate resistant 5-enolpyruvylshikimate-3-phosphate synthase (CP4 EPSPS) protein (U.S. Pat. No. 5,633,435) from *Agrobacterium* sp. strain CP4 that confers plant tolerance to glyphosate. a. "Glyphosate" refers to N-phosphonomethylglycine and its salts. N-phosphonomethylglycine is a well-known herbicide that has activity on a broad spectrum of plant species. Glyphosate is the active ingredient of Roundup® (Monsanto Co.), a safe herbicide having a desirably short half-life in the environment. Glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation containing glyphosate. Examples of commercial formulations of glyphosate include, without restriction, those sold by Monsanto Company as ROUNDUP®, ROUNDUP® ULTRA, ROUNDUP® ULTRAMAX, ROUNDUP® WEATHERMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Syngenta Crop Protection as TOUCHDOWN® herbicide, which contains glyphosate as its trimethylsulfonium salt. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants. Glyphosate tolerance can be achieved by the expression of bacterial EPSPS variants and plant EPSPS variants that have lower affinity for glyphosate and therefore retain their catalytic activity in the presence of glyphosate (U.S. Pat. Nos. 5,633,435, 5,094, 945, 4,535,060, and 6,040,497).

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a corn genome are not considered to be isolated from the corn genome so long as they are within the corn genome. However, each of these components, and subparts of these components, would be "isolated" within the scope of this disclosure so long as the structures and components are not within the corn genome.

For the purposes of this disclosure, any transgenic nucleotide sequence, i.e., the nucleotide sequence of the DNA inserted into the genome of the cells of the corn plant event MON87460 would be considered to be an isolated nucleotide sequence whether it is present within the plasmid used to transform corn cells from which the MON87460 event arose, within the genome of the event MON87460, present in detectable amounts in tissues, progeny, biological samples or commodity products derived from the event MON87460. The nucleotide sequence or any fragment derived therefrom would be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the event MON87460. For that matter, the junction sequences as set forth at SEQ ID NO:1 and SEQ ID NO:2, and nucleotide sequences derived from event MON87460 that also contain these junction sequences are considered to be isolated or isolatable, whether these sequences are present within the genome of the cells of event MON87460 or present in detectable amounts in tissues, progeny, biological samples or commodity products derived from the event MON87460.

As used herein, a transgene/genomic junction is the point at which heterologous DNA from a transformation vector that is inserted into the genome is linked to the corn plant genomic DNA. A junction polynucleotide spans the transgene/genomic junction, and is novel in any particular transgenic plant event. Thus, detection of a junction polynucleotide in a biological sample is diagnostic for the presence of a specific plant event. In the present invention, the presence of SEQ ID NO:1 through SEQ ID NO:4 junction polynucleotides in a sample is diagnostic for the presence of MON87460 DNA in a sample.

A "probe" is a polynucleotide to which is attached a conventional detectable label or reporter molecule, e.g., a radioactive isotope, ligand, chemiluminescent agent, or enzyme. Probes are complementary to a strand of a target nucleic acid, in the case of the present invention, to a strand of genomic DNA from MON87460, whether from a MON87460 plant or from a sample that includes MON87460 DNA. Probes according to the present invention include not only deoxyribonucleic or ribonucleic acids, but also polyamides and other probe materials that bind specifically to a target DNA sequence and can be used to detect the presence of that target DNA sequence.

DNA primers are isolated polynucleotides that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to two DNA primers useful for amplification of a target nucleic acid sequence, e.g., by the polymerase chain reaction (PCR) or other conventional polynucleotide amplification methods.

DNA probes and DNA primers are generally 11 polynucleotides or more in length, often 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Methods for preparing and using polynucleotide probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications,* Academic Press: San Diego, 1990. PCR DNA primer pairs can be derived from a known sequence, for example, by using computer programs intended for that purpose such as Primer (Version 0.5, © 1991, Whitehead Institute for Biomedical Research, Cambridge, Mass.).

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules, also referred to as nucleic acid segments, or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach,* IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology,* John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a polynucleotide of the present invention will specifically hybridize to one or more of the nucleic acid molecules set forth in SEQ ID NO: 1-7 or complements or fragments thereof under moderately stringent conditions, for example at about 2.0×SSC and about 65° C. In a particularly preferred embodiment, a nucleic acid of the present invention will specifically hybridize to one or more of the nucleic acid molecules set forth in SEQ ID NOs: 1-7 or complements or fragments thereof under high stringency conditions.

As used herein, "amplified DNA" or "amplicon" refers to the polynucleotides that are synthesized using amplification techniques, such as PCR. The term "amplicon" as used herein specifically excludes primer dimers that may be formed in a DNA amplification reaction.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

A member of a primer pair derived from the plant genomic sequence adjacent to the transgene insert DNA is located a distance from the inserted DNA sequence, this distance can range from one nucleotide base pair up to about twenty thousand nucleotide base pairs. Similarly, a member of a primer pair derived from the transgene insert DNA is located a distance from the plant genomic sequence junction, this distance can range from one nucleotide base pair up to about the full length of the transgene insert. The amplicon may range in length from the combined length of the primer pair plus one nucleotide base pair, but is preferably about fifty nucleotide base pairs or longer, for example, up to 500 or even 1000 nucleotides in length. Smaller sized amplicons in general are more reliably produced in PCR reactions, allow for shorter cycle times and can be easily separated and visualized on agarose gels or adapted for use in TaqMan assays, such as end-point and RealTime Taqman. Alternatively, a primer pair can be derived from genomic sequence on both sides of the inserted heterologous DNA so as to produce an amplicon that includes the entire insert polynucleotide sequence (e.g., a forward primer isolated from SEQ ID NO:5 and a reverse primer isolated from SEQ ID NO:6 that amplifies a DNA molecule comprising the pMON73608 DNA fragment that was inserted into the MON87460 genome, the insert comprising about 3309 nucleotides (SEQ ID NO:7), shown as capital letters in FIG. 3.

To determine whether a corn plant resulting from a sexual cross contains transgenic plant genomic DNA from the corn plant MON87460 plant of the present invention, DNA that is extracted from a corn plant tissue sample is subjected to a polynucleotide amplification method using a primer pair that includes a first primer derived from DNA sequence in the genome of the MON87460 plant adjacent to the insertion site of the inserted heterologous DNA (transgene DNA), and a second primer derived from the inserted heterologous DNA to produce an amplicon that is diagnostic for the presence of the MON87460 plant DNA. The diagnostic amplicon is of a specific length depending on the location of the primers, and comprises a specific junction polynucleotide sequence that is diagnostic for the specific plant event genomic DNA. The presence of the junction polynucleotide sequence in an amplicon can be determined, for example, by sequencing the amplicon DNA or by hybridization with a specific probe. In the present invention, the DNA sequence of the amplicon diagnostic for the presence of the MON87460 comprises SEQ ID NO:1 or SEQ ID NO:2. More specifically, in an embodiment of the present invention, an amplicon diagnostic for the presence of the MON87460 is 68 nt in length and comprises SEQ ID NO:2, and may be detected by hybridization with a labeled probe comprising any one of SEQ ID NO:2, SEQ ID NO:10 or SEQ ID NO:16.

Polynucleotide amplification can be accomplished by any of the various amplification methods known in the art, including the polymerase chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from MON87460 can be verified (and corrected if necessary) by amplifying such DNA molecules from the MON87460 seed or plants grown from the seed deposited with the ATCC having accession no. PTA-8910, using primers derived from the sequences provided herein, followed by standard DNA sequencing of the PCR amplicon or cloned DNA fragments thereof. Corn seeds containing the MON87460 transgenic insert were deposited with the American Type Culture Collection, 10801 University Blvd, Manassas, Va. 20110 on Feb. 1, 2008 under ATCC Accession No. PTA-8910.

DNA detection kits that are based on DNA amplification methods contain DNA primer molecules that hybridize specifically to a target DNA and amplify a diagnostic amplicon under the appropriate reaction conditions. Any length amplicon produced from MON87460 DNA wherein the amplicon comprises SEQ ID NO:1 or SEQ ID NO:2 is an aspect of the invention. The skilled artisan will recognize that the first and second DNA primer molecules are not required to consist only of DNA but may also be comprised exclusively of RNA, a mixture of DNA and RNA, or a combination of DNA, RNA, or other nucleotides or analogues thereof that do not act as templates for one or more polymerases. In addition, the skilled artisan will recognize that a probe or a primer as set forth herein shall be at least from about 11, 12, 13, 14, 15, 16, 17, 18, 19, and 20 consecutive nucleotides in length and selected from the group of nucleotides as set forth in SEQ ID NO:1 and SEQ ID NO:3 (arbitrarily designated 5' junction), SEQ ID NO:2 and SEQ ID NO:4 (arbitrarily designated 3' junction), SEQ ID NO:5 (arbitrarily designated 5' flanking sequence), SEQ ID NO:6 (arbitrarily designated 3' flanking sequence), and SEQ ID NO:7 (inserted transgene sequence). Probes and primers at least from about 21 to about 50 or more consecutive nucleotides in length are possible when selected from the group of nucleotides as set forth in SEQ ID NO:5 through SEQ ID NO:7.

The kit may provide an agarose gel based detection method or any number of methods of detecting the diagnostic amplicon that are known in the art. A kit that contains DNA primers that are homologous or complementary to any portion of the corn genomic region of SEQ ID NO:5 or SEQ ID NO:6 and to any portion of the transgene insert region of SEQ ID NO:7 is an object of the invention. Specifically identified as a useful primer pair in a DNA amplification method is SEQ ID NO:8 and SEQ ID NO:9 that amplify a diagnostic amplicon homologous to a portion of the 5' transgene/genome region of MON87460, wherein the amplicon comprises SEQ ID NO:2. Other DNA molecules useful as DNA primers can be selected from the disclosed transgene/genomic DNA sequence of MON87460 by those skilled in the art of DNA amplification.

The diagnostic amplicon produced by these methods may be detected by a plurality of techniques. One such method is Genetic Bit Analysis (Nikiforov, et al. Nucleic Acid Res.

22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully described in the instructions provided by the manufacturer. Briefly, a FRET (fluorescence resonance energy transfer) oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety, such as 6FAM™ and VIC™, away from the quenching dye, such as TAMRA (tetramethyl-6-carboxyrhodamine) for conventional probes, or non-fluorescent minor groove binding compounds for MGB probes. With either TAMRA or MGB probes, the polymerase cleaves bound probe during PCR, separating the fluorophore and quencher to the extent that FRET cannot occur, and a fluorescent signal indicates the presence of the transgene/genomic sequence.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal indicates the presence of the flanking/transgene insert sequence due to successful amplification and hybridization.

Other described methods, such as microfluidics (U.S. Patent Publication No. 2006068398, U.S. Pat. No. 6,544, 734) may be used to separate and amplify DNA samples. Optical dyes are used to detect and quantitate specific DNA molecules (WO/05017181). Nanotube devices have been described (WO/06024023) that comprise an electronic sensor for the detection of DNA molecules or nanobeads that bind specific DNA molecules.

DNA detection kits can be developed using the compositions disclosed herein and the methods well known in the art of DNA detection. The kits are useful for identification of corn plant MON87460 DNA in a sample and can be applied to methods for breeding corn plants containing MON87460 DNA. A kit contains DNA molecules that are useful as primers or probes and that are homologous or complementary to at least a portion of SEQ ID NO:1-7. The DNA molecules can be used in DNA amplification methods (PCR) or as probes in nucleic acid hybridization methods such as Southern analysis and northern analysis.

In another aspect of the present invention, a preferred polynucleotide of the present invention that is diagnostic for the presence of MON87460 DNA has the sequence set forth in SEQ ID NO:1 through SEQ ID NO:4, or SEQ ID NO:25. SEQ ID NO:1 through SEQ ID NO:4 and larger genomic/transgene junction polynucleotides, such as those in SEQ ID NO: 5-7 may also be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY. The hybridization of the probe to the target DNA molecule can be detected by any number of methods known to those skilled in the art, these can include, but are not limited to, fluorescent tags, radioactive tags, antibody based tags, and chemiluminescent tags. In another aspect of the present invention, a preferred marker nucleic acid molecule of the present invention shares between 80% and 100% or 90% and 100% sequence identity with a nucleic acid sequence set forth in SEQ ID NO:1 through SEQ ID NO:7 or complements thereof or fragments of either. In a further aspect of the present invention, a preferred marker nucleic acid molecule of the present invention shares between 95% and 100% sequence identity with a sequence set forth in SEQ ID NO:1 through SEQ ID NO:7 or complements thereof or fragments of either.

Water deficit tolerant corn plants that lack a selectable marker gene or lack an intact selectable marker gene also provided herein. Such plants can be obtained by methods that comprise exposing a corn chromosome comprising a heterologous transgene insert that confers water deficit tolerance and a selectable marker gene to one or more recombination-inducing agents and selecting a corn plant comprising a heterologous transgene insert that confers water deficit tolerance where the selectable marker gene has been either completely or partially eliminated or where the selectable marker gene has been disrupted. Heterologous transgene inserts that confer water deficit tolerance and contain a selectable marker include, but are not limited to, inserts comprising SEQ ID NO:7 or inserts comprising SEQ ID NO:1, a truncated rice actin promoter that is operably linked to a cspB gene, a selectable marker gene, and SEQ ID NO:2. Corn chromosomes that comprising a heterologous transgene insert that confers water deficit tolerance and a selectable marker gene also include, but are not limited to, a corn chromosome that comprises SEQ ID NO:24, a corn chromosome of a corn plant having been deposited under ATCC Accession No. PTA-8910 (ATCC, 10801 University Blvd., Manassas, Va., USA), and progeny thereof. Heterologous transgene inserts that confer water deficit tolerance include, but are not limited to, inserts comprising SEQ ID NO:1 and a truncated rice actin promoter that is operably linked to a cspB gene as well as inserts comprising SEQ ID NO:1 and a truncated rice actin promoter that is operably linked to a cspB gene where a 5' terminus of the insert overlaps a 3' terminus of SEQ ID NO:1.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions (i.e., T-DNA border sequences, site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, target sequences for site specific recombinases) and sequences that provide replication functions (i.e., bacterial origins of replication, autonomous replication sequences, centromeric sequences).

Recombination inducing agents can comprise ionizing radiation and/or any compound, protein, and/or a nucleic acid that provides for elimination or modification of a polynucleotide sequence. Recombination inducing agents thus include, but are not limited to, agents that provide for homologous recombination, non-homologous recombination, site-specific recombination, and/or genomic modifications. Genomic modifications provided by recombination inducing agents thus include, but are not limited to, insertions, deletions, inversions, and/or nucleotide substitutions. Use of recombination inducing agents to induce genetic modifications in plants has been disclosed (Lloyd et al., Proc Natl Acad Sci USA., 102(6):2232, 2005). Recombination agents can be native or engineered. Site specific recombinases include, but are not limited to, a Cre-recombinase, a FLP recombinase, a Flippase and the like. Recombination-inducing agents also include, but are not limited to nucleases. Nucleases that can be used include, but are not limited to, meganucleases and zinc-finger nucleases. Other recombination-inducing agents include, but are not limited to, homologous replacement sequences and non-homologous replacement sequences. In certain embodiments, recombination-inducing reagents can comprise a nuclease and a homologous or non-homologous replacement sequence. In certain embodiments, a cre-recombinase capable of excising the selectable marker located between the lox sites of SEQ ID NO:24 can be used. Cre-mediated elimination of sequences flanked by lox sites in plants has been disclosed (U.S. Pat. No. 5,658,772).

Elimination or disruption of a selectable marker gene, a portion thereof, or other sequence can be effected by inducing a double stranded break in the target sequence, providing a homologous replacement sequence that lacks the selectable marker gene or a portion thereof, and recovering plants where the replacement sequence has integrated in place of the originally resident sequences. A homologous replacement sequence can comprise homologous sequences at both ends of the double stranded break that are provide for homologous recombination and substitution of the resident sequence in the chromosome with the replacement sequence. Targeted double-strand break-induced homologous recombination in crop plants such as tobacco and maize has been disclosed (Wright et al., Plant J. 44, 693, 2005; D'Halluin, et al., Plant Biotech. J. 6:93, 2008). It is also possible to insert a homologous replacement sequence into a targeted nuclease cleavage site by non-homologous end joining or a combination of non-homologous end joining and homologous recombination (reviewed in Puchta, J. Exp. Bot. 56, 1, 2005). Targeted insertion of homologous replacement sequences into specific plant genomic sites by non-homologous end joining or a combination of non-homologous end joining and homologous recombination has also been disclosed (Wright et al., Plant J. 44, 693, 2005). In certain embodiments, a meganuclease that catalyzes at least one site specific double stranded break in the selectable marker gene can be used. Meganucleases have been shown to be amenable to genetic modification such that they can be evolved or engineered (WO/06097853A1, WO/06097784A1, WO/04067736A2) or rationally designed (U.S. 20070117128A1) to cut within a recognition sequence that exactly matches or is closely related to specific target sequence. In these cases, given a reasonably sized target such as a selectable marker gene sequence, one can select or design a nuclease that will cut within the target selectable marker gene sequence. Alternatively, a zinc finger nuclease that that catalyzes at least one site specific double stranded break in the selectable marker gene can be used. Such zinc-finger nucleases, the ability to engineer specific zinc-finger nucleases, and their use in providing for homologous recombination in plants have also been disclosed (WO 03/080809, WO 05/014791, WO 07014275, WO 08/021207).

Elimination or disruption of a selectable marker gene, a portion thereof, or other sequence can also be effected by inducing a double stranded break in the target sequence, providing a non-homologous replacement sequence that lacks the selectable marker gene or a portion thereof, and recovering plants where the non-homologous replacement sequence has integrated in the target sequence. In certain embodiments, a non-homologous replacement sequence can comprise single stranded sequences at both ends that are complementary to single stranded sequences at both ends of the double stranded break to provide for non-homologous end joining of the replacement sequence and double stranded break.

Methods for de novo generation of a corn plant that is substantially equivalent to a corn plant of event MON87460 and resultant plants are also provided herein. Such methods can comprise use of recombination-inducing agents. Corn plants that are substantially equivalent to a corn plant of event MON87460 include, but are not limited to, corn plants comprising a chromosome having a heterologous transgenic insert comprising a promoter that is operably linked to a cspB gene, where the transgenic insert is present at the same or substantially the same chromosomal location or chromosomal integration site as in MON87460. Promoters that can be operably linked to a cspB gene, include, but are not limited to, rice actin promoters, including truncated rice actin promoters, a maize RS81 promoter, a maize RS324 promoter, a maize A3 promoter, viral promoters, and the like. In certain non-limiting embodiments, one can select, evolve or design a nuclease to cut within a target recognition sequence that exactly matches or is closely related to a target sequence in SEQ ID NO:5, in SEQ ID NO:6, in a corn chromosomal sequence that spans SEQ ID NO:5 and SEQ ID NO:6 in a non-transgenic corn plant, or in SEQ ID NO:23. In these or other non-limiting embodiments, a genetically-modified corn plant which contains a promoter operably linked to a cspB gene can be produced by: i) introducing into a corn plant cell a homologous replacement sequence comprising a promoter that is operably linked to a cspB gene and flanking sequences that are substantially identical to a target sequence and a nuclease that cleaves the target sequence; and ii) selecting for a corn cell or corn plant where the homologous replacement sequence has integrated into the target sequence. Given that corn chromosomal target sequences disclosed herein have been found to be favorable sites for transgene insertion, methods for obtaining plants with insertions of one or more transgenes that confer traits other than water deficit tolerance or transgenes that comprise genes other than cspB that confer water deficit tolerance into target sites disclosed herein are also provided.

The availability of recombination-inducing agents and various homologous replacement sequences also provides for water deficit tolerant corn plants that comprise one or more additional gene(s) integrated into the same chromosomal location as the heterologous transgene insert that confers water deficit tolerance. Integration of the additional genes at the same location as the gene that confers water deficit tolerance is advantageous in that any traits carried by the additional genes will be genetically linked to the water deficit tolerance trait, thus facilitating breeding. In certain embodiments, an additional gene or genes can be a gene or genes that work in concert with the resident heterologous transgene insert that confers water deficit tolerance to provide additional water deficit tolerance. In certain embodiments, an additional gene or genes can be a gene or genes that provide a distinct and useful trait other than water deficit tolerance. Thus, one or more genes that confer one or more traits include, but are not limited to, genes that confer herbicide resistance, pest resistance, improved yield under water sufficient conditions, improved seed oil, improved seed starch, improved seed protein, and/or improved nitrogen utilization. Such plants can be obtained by methods that comprise exposing a corn chromosome comprising a heterologous transgene insert that confers water deficit tolerance to a homologous replacement sequence comprising one or more additional genes and selecting a corn plant comprising a heterologous transgene insert that confers water deficit tolerance and one or more additional genes. In certain embodiments, the insertion of the homologous replacement sequence can be facilitated by use of an additional recombination-inducing agent. Additional recombination-inducing agents used include thus include, but are not limited to, a meganuclease, a zinc-finger nuclease, or other agent that induces a double-stranded break at a desired site of double-strand break-induced homologous recombination. Heterologous transgene inserts that confer water deficit tolerance include, but are not limited to, inserts comprising SEQ ID NO:1 and a truncated rice actin promoter that is operably linked to a cspB gene as well as inserts comprising SEQ ID NO:1 and a truncated rice actin promoter that is operably linked to a cspB gene where a 5' terminus of the insert overlaps a 3' terminus of SEQ ID NO:1. In certain embodiments, the homologous replacement sequence comprises a sequence that provides for replacement of a selectable marker gene that is in a resident heterologous transgene insert with one or more additional genes. Heterologous transgene inserts that confer water deficit tolerance and contain a selectable marker include, but are not limited to, inserts comprising SEQ ID NO:7 or inserts comprising SEQ ID NO:1 and a truncated rice actin promoter that is operably linked to a cspB gene. Corn chromosomes that comprise a heterologous transgene insert that confers water deficit tolerance and a selectable marker gene also include, but are not limited to, a corn chromosome that comprises SEQ ID NO:24, a corn chromosome of corn plant having been deposited under ATCC Accession No. PTA-8910, and progeny thereof. In certain embodiments, an additional gene or gene can also be inserted into SEQ ID NO:5 and/or SEQ ID NO:6.

It is also anticipated that any of the aforementioned additional gene or genes can be integrated into a chromosome comprising SEQ ID NO:1 and a truncated rice actin promoter that is operably linked to a cspB gene and one or more lox sites by site specific recombination. Site specific recombination systems used for this purpose include, but are not limited, to FLP recombinase/FRT, cre recombinase/lox, and combinations thereof. The use of site-specific recombination systems in plants and other eukaryotic organisms has been disclosed (U.S. Pat. Nos. 5,801,030, 5,658,772, and 6,262,341). The presence of lox site specific recombination sites in corn chromosomes comprising SEQ ID NO:7 or SEQ ID NO:24 and a corn chromosome of a corn plant having been deposited under ATCC Accession No. PTA-8910, and progeny thereof, thus provides for site specific integration of additional genes into these corn chromosomes. In certain embodiments, the selectable marker sequence which is flanked by the lox sites in the corn chromosomes is first excised by cre-recombinase, leaving a single lox site in the chromosome. Additional genes can then be introduced on a circular DNA molecule comprising the additional genes and an operably linked lox site and integrated into the corn chromosome at the single lox site that was left in the chromosome. Exemplary schemes for creating circular DNA molecules and site-specific integration of genes into chromosomes have been disclosed (Vergunst et al., Nucleic Acid Res. 26(11), 279, 1998). Introduction of site-specific recombination sites other than lox at the chromosomal location of the SEQ ID NO:24 insertion and insertion of additional genes at those recombination sites is also provided herein.

The following examples are included to demonstrate examples of certain preferred embodiments of the invention. It should be appreciated by those of skill in the art that the techniques disclosed in the examples that follow represent approaches the inventors have found to function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1 Production of Transgenic Corn Plants

Transgenic corn plants were produced by *Agrobacterium*. mediated transformation of LH59 corn with the vector pMON73608 (FIG. 1). This vector contains the cspB coding region regulated by the rice actin promoter, the rice actin intron, and the tr7 3' polyadenylation sequence, and the nptII coding region regulated by the 35S CaMV promoter, and the NOS 3' polyadenylation sequence.

*Agrobacterium* was prepared via standard methods and 50 to 100 pieces of callus were transferred to a Petri dish containing about 15 ml of *Agrobacterium* suspension at 0.1 to 1.0×109 cfu/ml. Callus pieces, 2 mm to 8 mm in diameter, were incubated for about 30 minutes at room temperature with the *Agrobacterium* suspension, followed by removal of the liquid by aspiration. About 50 uL of sterile distilled water was added to filter paper in a 60×20 mm Petri dish. Fifteen to 20 pieces of inoculated callus were transferred to each filter paper and the plate sealed. The callus and *Agrobacterium* were co-cultured for about 3 days at 23° C. in the dark.

Calli were transferred from filter paper to medium callus initiation medium containing carbenicillin and cultured in the dark at 27° C. to 28° C. for 2-5 days. Selection was initiated by transferring callus to callus initiation medium containing silver nitrate, carbenicillin and mg/L paromomycin. After 2 weeks culture in the dark at 27° C. to 28° C., callus was transferred to medium containing higher levels of paromomycin. Callus was subcultured after two weeks to fresh medium and further cultured for two weeks in the dark at 27° C. to 28° C. Callus was then transferred to again to medium with higher levels of paromomycin. After 2-3 weeks culture in the dark at 27° C. to 28° C., paromomycin resistant callus was identified.

Plants were regenerated (RO plants) from transformed callus, transferred to soil and grown in the greenhouse. RO plants were screened by PCR for presence of the cspB and

TABLE 1

Summary of Genetic Elements in pMON73608

| Genetic Element | Position in FIG. 1 | Function (Reference) |
| --- | --- | --- |
| CR-Ec.rop-1:1:3 | 53-244 | Coding sequence for repressor of primer protein |
| OR-Ec.ori-ColE1-1:1:1 | 672-1260 | Origin of replication from pBR322 for maintenance of plasmid in *E. coli* |
| P-Ec.aadA-SPC/STR-1:1:1<br>CR-Ec.aadA-SPC/STR-1:1:3<br>T-Ec.aadA-SPC/STR-1:1:1 | 1793-2681 | Bacterial promoter and coding sequence for an aminoglycoside-modifying enzyme, 3'(9)-Onucleotidyltransferase from the transposon Tn7 (GenBank accession X03043) |
| B-AGRtu.right border-1:1:12 | 2816-3172 | Right border sequence essential for transfer of T-DNA derived from *Agrobacterium* |
| P-Os.Act1-1:1:8 | 3205-4048 | Promoter, leader and intron from the rice actin gene |
| L-Os.Act1-1:1:5 | 4049-4128 | |
| I-Os.Act1-1:1:3 | 4129-4605 | |
| CR-Bs.cspB-1:4:1 | 4608-4811 | Coding region for the CSPB protein from *Bacillus subtilis* which a change in the second amino acid position from leucine to valine (WO05033318) |
| T-AGRtu.tr7-1:1:5 | 4842-5349 | 3' nontranslated region of the transcript 7 coding sequence from *Agrobacterium* that directs polyadenylation |
| RS-P1.lox1-1:1:1 | 5424-5457 | Recombination site recognized by Cre recombinase |
| P-CaMV.35S-1:1:6 | 5484-5776 | Cauliflower mosaic virus (CaMV) promoter |
| CR-Ec.nptII-Tn5-1:1:3 | 5841-6635 | Coding region isolated from Tn5 which codes for neomycin phosphotransferase type II. Expression of this gene in plant cells confers resistance to kanamycin and serves as a selectable marker for transformation |
| T-AGRtu.nos-1:1:13 | 6667-6919 | 3' nontranslated region of the nopaline synthase (NOS) coding sequence from *Agrobacterium tumifaciens* that directs polyadenylation |
| RS-P1.lox1-1:1:1 | 6945-6978 | Recombination site recognized by Cre recombinase |
| B-AGRtu.left border-1:1:5 | 6999-7440 | Left border sequence essential for transfer of T-DNA derived from *Agrobacterium* |
| OR-Ec.oriV-RK2-1:1:6 | 7527-7923 | Origin of replication for *Agrobacterium* derived from the broad host range plasmid RK2 |

LH59 callus was initiated from immature embryos. Immature embryos, 1.5 mm to 2.0 mm, were excised from developing maize plants and cultured with the embryonic axis side down on callus initiation medium for 8-21 days.

nptII coding regions, and Southern analysis was conducted to determine insert copy. Taqman analysis was used to determine presence or absence of vector backbone sequences. Transgenic events that were positive for the presence of both cspB and nptII genes, negative for the presence of vector backbone sequences and had one or two inserts (integration sites within the corn genome) were selected for physiological analysis for drought tolerance. The positive events were grown in the greenhouse to maturity and selfed. Homozygous, heterozygous, and non-transgenic seed from multiple transgenic events obtained by genomic insertions of the T-DNA of pMON73608 were collected from the selfed positive plants.

Example 2 Greenhouse Screening for Water Deficit Stress Tolerance

Transgenic heterozygous corn plants were grown from the heterozygous seed from transgenic events transformed with pMON73608 (Example 1) and screened for water deficit stress tolerance as compared to control plants by a high-throughput method of greenhouse screening in which water is withheld to create a "drought treatment". Water use efficiency is measured by plant growth rate, e.g., at least a 10% improvement, in height and biomass during a drought treatment, as compared to control plants. The hydration status of the shoot tissues following the drought is also measured. Shoot Initial Height (SIH) is plant height after 3 weeks of growth under optimum conditions. Shoot Wilt Height (SWH) is plant height at the end of a 6 day drought. Time course experiments have shown that at about 3 days of drought treatment, wild type corn plants basically stop growing and begin to wilt. Thus, a transgenic corn plant with improved water use efficiency will continue to grow (although possibly to a lesser extent than with water) and thereby be significantly taller at the end of a drought experiment. Shoot Wilt Mass (SWM) is the amount of wet and dry matter in the shoot (plant separated from root ball at the soil line) at the end of the drought; SDM is measured after 2 to 3 weeks in a drying chamber. Shoot Turgid mass (STM) is the SWM plus the mass of the water that is transported into plant tissues in 3 days of soaking in 40 degree Celsius water in the dark. Experiments have shown that most of the water is pulled up in 24 hours but it takes 2 more days before additional increase becomes insignificant. STM–SWM is indicative of water use efficiency in plants where recovery from stress is more important than stress tolerance per se. Relative water content (RWC) is a measurement of how much (%) of the plant is water at harvest. RWC=(SWM–SDM)/(STM–SDM)×100. Fully watered corn plants are about 98% RWC. Typically, in a wilt screen the plants are about 60% RWC. Plants with higher RWC at the end of a drought are considered to be healthier plants and more fit for post-drought recovery and growth. Relative Growth Rate (RGR) is calculated for each shoot using the formula

RGR=(SWH–SIH)/((SWH+SIH)/2)×100.

Transgenic heterozygous corn plants from multiple transgenic events comprising T-DNA of pMON73608, including MON87460, exhibited enhanced water deficit stress tolerance as compared to control plants.

Example 3 Improved Field Performance of MON87460 Corn Plants Under Water Deficit Water-limited field trials were performed using commercial grade hybrid corn in environments which received no rainfall during the target period for the water-deficit treatment, a span of 10 to 14 days immediately prior to flowering.

Two row plots, of 34 plants per row were planted at a density of 32,000 plants per acre in a western Kansas location. Each transgenic plot was paired with a non-transgenic plot of the same hybrid background. Twelve paired-plot replicates of each of 21 independent insertion events, and its non-transgenic pair, were planted in a randomized block design. Plants were maintained in a well-watered condition using overhead irrigation until the V8 stage of development, at which time water was withheld for a 14 day period.

On the 7th day of the water-withholding treatment the distance from the soil surface to the tip of the youngest fully extended leaf was determined for each of 3 transgene positive and transgene negative plants in each paired plot. This measurement was repeated 5 days later using the same leaf as on day 7. From the day 7 and day 12 measurements a growth rate, in cm/d, was calculated for each plant measured. This rate is referred to as Leaf Extension Rate (LER).

On the $8^{th}$ day of the treatment an estimate of chlorophyll content was made using the Minolta SPAD-502 (Spectrum Technologies, Plainfield, Ill.). This measurement was taken at a mid-leaf (base to tip) position of the youngest fully expanded leaf for 6 of the 21 events. SPAD readings were collected for each of 6 transgenic positive and 6 transgenic negative plants in each paired plot, for each paired plot replicate.

Similarly, on the $8^{th}$ day of the treatment, photosynthetic rates were measured at mid-day, using the mid-leaf of the youngest fully expanded leaf for the same 6 of the 21 events. Photosynthetic rates were measured using the PP Systems (Amesbury, Mass.) Ciras-1 Portable Photosynthesis System. Leaf photosynthesis was measured at an atmospheric $[CO^2]$ of 367 mol·mol$^{-1}$, an ambient water vapor pressure of 2.3 kPa, and a leaf air vapor pressure deficit between 0.6 and 1.5 kPa, with photosynthetic photon flux density between 1,200 and 1,400 mol·m$^{-2}$·s$^{-1}$.

Twenty-two CspB events were evaluated in the Kansas field trial. The water-deficit treatment resulted in an average reduction in growth rates to 50% of the well-watered rate. As a construct, the CspB transgenics demonstrated a 3.6% increase in leaf extension rates relative to non-transgenic controls (Table 2). MON87460 and a second high performing event demonstrated growth rate increases of 12 and 24%. The CspB positive plants also demonstrated significant improvements in chlorophyll content and photosynthetic rates (Table 2). At a construct level, chlorophyll content was increased by 2.5%, with MON87460 and a second high performing event exhibiting increases of 4.4 and 3.3%. The improvements to the photosynthetic rates were 3.6% at a construct level, with increases of 8.5 and 7.7% for MON87460 and a second high performing event.

TABLE 2

Improved Growth of cspB events Under Field Water-Deficit Conditions

| Gene-Event | % Increase LER (field) | % increase Chlorophyll content | % Increase Photosynthesis |
|---|---|---|---|
| CspB-Construct | 3.6% | 2.5% | 3.6% |
| CspB-Zm Event MON87460 | 12% | 4.4% | 8.5% |
| CspB-Zm Event 2 | 24% | 3.3% | 7.7% |

Example 4 Improved Yield of MON87460 Corn Plants Under Limited-Water Treatment

The yield performance of 10 independently integrated CspB events, most of which had previously demonstrated improved vegetative performance in either greenhouse screens or field trials, was evaluated in an elite hybrid genetic background at 4 locations in central California where a limited-water treatment was applied. Water-limited treatment was applied by reducing irrigation for a 14 day period during the late vegetative stage of development, immediately prior to flowering. The treatment resulted in a net reduction of approximately 49.2 cm$^3$ of water relative to a well-watered regime. This was achieved by omitting two of three 24.6 cm$^3$ applications of water during the stress period. The treatment reduced the relative growth rate during the treatment by approximately 50% of well-watered rates and similarly reduced the average end of season grain yield by 50%. Each trial location was designed as a 4-factor group unbalanced block design, and planted with 3 replications per location. Within each replication, the genotypes were randomized as the 1$^{st}$ factor, and constructs, events, and gene-positive vs. gene-negative plots were randomized as the 2$^{nd}$, 3$^{rd}$, and 4$^{th}$ factors, respectively. The design placed the positive and negative entries for each selection in adjacent 2 row plots. Final population density reflected local planting practices and ranged from 65 to 76 plants per 2 row plot. Plots were 21 feet long and row spacing ranged from 30 to 40 inches wide, reflecting local planting practices.

Grain yield data was collected from the water-limited field trials and is provided in Table 3 below. Mean yield at the water-limited California fields was 6.8 t/Ha, representing a 50% reduction in yield relative to the average mean yield of crops in the Midwest. Yield averages of CspB positive plants as a construct, were significantly greater, by 7.5% ($p<0.01$). A number of individual events exhibited significant yield advantages as well. CspB-Zm MON87460 was the best performing event and demonstrated a yield improvement of 20.4%.

TABLE 3

Improved Yield of cspB events Under Field Water-Limited Conditions

| Event | Yield (t/Ha) | % improvement |
| --- | --- | --- |
| CspB Non-transgenic Mean | 6.86 | |
| CspB-Construct Mean | 7.38 | 7.5% |
| CspB-Zm Event MON87460 | 8.26 | 20.4% |
| CspB-Zm Event 2 | 7.61 | 10.9% |

The MON87460 event also demonstrated significant improvements in leaf growth, chlorophyll content and photosynthetic rates, providing evidence that these improvements in vegetative productivity translate into improvements in reproductive performance and grain yield, and identifying MON87460 as the top performer among the multiple independent transgenic events tested in greenhouse or field studies.

Example 5 Molecular Analysis

MON87460 was characterized by detailed molecular analyses, including screens for insert number (number of integration sites within the corn genome), copy number (the number of copies of the T-DNA within one locus), the integrity of the inserted cassettes and the absence of backbone sequence.
Southern Blot Analyses Approximately 2-3 g leaf tissue was dried in a lyophilizer for ~48 hours by adding small metal beads and shaking in a paint shaker. Each sample was mixed with 6 ml extraction buffer (0.1M Tris pH 8, 0.05 M EDTA, 0.5M NaCl, 1% SDS with 0.071% BME added fresh), placed in a 65° C. water bath for 45 minutes, and mixed occasionally. Potassium acetate, 5M (2 ml) was added, the tubes were then inverted two times and transferred to an ice bath for 20 minutes. Cold chloroform (3 ml) was added and mixed gently by inversion for 10 minutes. Samples were centrifuged at 3500 rpm for 15 minutes. The supernatant was transferred to new tubes and combined with 4 ml cold isopropanol. Samples were centrifuged at 3500 rpm for 15 minutes and the supernatant discarded. The pellet was resuspended in 2 ml $T_{50}E_{10}$ buffer with 0.1 mg/ml RNAse and incubated at 65° C. for 20 minutes. To precipitate the DNA, 3 ml isopropanol/4.4M ammonium acetate (7:1) were added to each tube and inverted to mix. Samples were centrifuged at 3500 rpm for 15 minutes and the supernatant was discarded. The pellets were rinsed with 0.5-1.0 ml 80% EtOH then transferred to microcentrifuge tubes. After a brief spin in a microcentrifuge the supernatant was discarded and the pellets were allowed to air-dry. Pellets were resuspended in ~200 µl TE buffer.

Approximately 10 µg of genomic DNA was digested using 100 units of various restriction enzymes in a total volume of 500 µl. Digests were incubated at 37° C. overnight and EtOH precipitated. The digested DNA was then pelleted and re-dissolved in 20 µl TE buffer. DNA probe templates were prepared by PCR amplification of plasmid pMON73608. Approximately 25 ng of each probe was labeled with ~100 µCi of $^{32}$P-dCTP (Amersham catalog # AA0075) using random priming (Radprime® DNA labeling System, Invitrogen). Radiolabeled probes were purified using a Sephadex G-50 column (Roche). Samples were loaded onto 0.8% TAE gels and run 14-18 hours at 30-35V. After electrophoresis, the gels were stained in 1.5 µg/ml ethidium bromide for 10-15 minutes and then photographed. The gels were then placed in depurination solution (0.125 N HCl) for 10-15 minutes followed by a denaturing solution (0.5M NaOH, 1.5 M NaCl) for 30-40 minutes and then a neutralizing solution (0.5M Tris-HCl pH 7.0, 1.5 M NaCl) for 30-40 minutes. The gels were then transferred to a 20×SSC solution for 5-15 minutes. Capillary transfer of DNA (Southern, 1975) onto Hybond-N nylon membrane (Amersham) was facilitated overnight using a Turboblotter™ (Schleicher & Schuell) with 20×SSC transfer buffer. DNA was covalently cross-linked to the membrane with a UV Stratalinker® 1800 (Stratagene) using the auto-crosslink setting and stored at 4° C. until required. Membranes were incubated for 1-4 hours at 60-65° C. in prehybridization buffer (250 mM Na$_2$HPO$_4$.7H2O pH 7.2, 7% SDS, and 0.1 mg/ml tRNA). The $^{32}$P-labeled probe was added to fresh prehybridization buffer and hybridized overnight at 60-65° C. Membranes were washed 3 times in an aqueous solution of 0.1% SDS and 0.1×SSC for 15-20 minutes.

Probes included the intact cspB and nptII coding regions and their respective promoters, introns, and polyadenylation sequences and the plasmid backbone. No additional elements from the original transformation vector, linked or unlinked to the intact cassettes, were identified in the genome of these corn events. No backbone sequence was detected.

The data show that corn event MON87460 contains a single T-DNA insertion with one copy of the cspB and nptII cassettes.

Results from reactions using rice actin promoter and intron sequence probes indicated that the full rice actin promoter sequence present in pMON73608 is not present in MON87460. The rice actin intron element was confirmed to be intact in MON87460.

Northern Blot Analyses

RNA from corn event MON87460 and wild type leaf tissue from greenhouse grown plants was isolated from one gram tissue samples using a ToTALLY RNA™ Kit (Ambion catalog #1910). Samples containing 5, 10, 25 and 50 µg MON87460 and wild type RNA were prepared and run on a 1.0% agarose gel at 120V for approximately 2 hours. Following electrophoresis, the gels were then rinsed in deionized $H_2O$ blotted to nylon membranes. The gels were allowed to transfer overnight. The blots were covalently cross-linked and placed at 4° C. for short-term storage. Prior to prehybridization, the blots were pre-rinsed in 10×SSC for 2 minutes. The bots were then placed in individual hybridization bottles with 20 ml Sigma Hyb Buffer (catalog # H7033) and prehybridized at 65° C. for 1 hour.

Approximately 25 ng of cspB and nptII probe templates were labeled with ~50 µCi of $^{32}$P-dCTP using random priming (Radprime® DNA labeling System, Invitrogen). Denatured cspB and nptII radiolabeled probes were then added to separate tubes containing 5 ml preheated hybridization buffer. The buffer containing each probe was then mixed and added to the appropriate hybridization bottle and hybridized overnight. Following an overnight hybridization the blots were removed from the bottle and placed in low stringency wash buffer (2×SSC, 0.1% SDS) in a glass tray and placed on a shaker for 10 minutes at room temperature. The blots were placed on blotting paper and then in fresh hybridization bottles with 25 ml of low stringency pre-warmed wash buffer (65° C.). The blots were washed at 65° C., two times in low stringency wash buffer for 15 minutes and once at 65° C., in high stringency wash buffer (0.5×SSC, 0.1% SDS) for 15 minutes.

Northern blot analysis confirmed that the expected size transcripts for both cspB (~600 nt) and nptII (~1100 nt) are generated in MON87460.

Sequencing T-DNA Insert and Flanking Corn Genomic DNA in Lambda Clone

High quality genomic DNA from corn event MON87460 was isolated using an SDS chloroform extraction method. MON87460 genomic DNA was digested with MfeI and purified using the QIAEX® II Gel Extraction Kit (Qiagen), to ensure the purification of fragments greater than 10 kb. This digested and purified genomic DNA was used for ligation into the Lambda DASH® II/EcoRI Vector Kit (Stratagene). Approximately 2.5×10$^5$ colonies were screened using $^{32}$P-labeled Ract intron and cspB probes. Purified DNA from a pure bacteriophage lambda clone was used as template in sequencing reactions to confirm the T-DNA nucleotide sequence of the MON87460 insert and corn genomic DNA flanking the 5' and 3' ends of the MON87460 insert.

DNA sequence analysis confirms that the in planta T-DNA in MON87460 is identical to the corresponding sequence in pMON73608. This sequence analysis also characterized the extent of the truncation of the 5' end of the rice actin promoter which had been observed in Southern analysis. The sequence analysis revealed that the *Agrobacterium* RB and most of the P-ract promoter are not present in the MON87460 event. The P-ract promoter in MON87460 consists of only 108 bp of the 3' end of the full rice actin promoter region (Δ850 nt) in pMON73608. This result also confirms that the in planta sequence for cspB and nptII in corn event MON87460 match the exact coding regions within the transformation vector pMON73608. This clone also confirmed 1060 bp of 5' flanking sequence, 3309 bp of T-DNA insert and 1260 bp of 3' flanking sequence for the MON87460 insert.

Wildtype Allele Analysis

PCR was performed on genomic DNA from the nontransgenic corn line used in transformation using primers that hybridize to the 5' and 3' flanking regions of the MON87460 insert. Multiple primer combinations were performed with each combination consisting of a primer that hybridizes to the 5' and 3' flanking region, respectively. The PCR analysis was performed using ~50 ng of genomic DNA template in a 50 µl reaction volume. Resulting amplicons were then sequenced. Analysis of the wild type allele showed that a 22 bp deletion of corn genomic DNA (SEQ ID NO:23) occurred upon integration of the MON87460 T-DNA into the corn chromosome.

Example 6 Detection of MON87460 Event Polynucleotides

The detection of MON87460 event in progeny resulting from breeding with a MON87460 line may be accomplished by extraction of genomic DNA from corn plant tissues and analysis for MON87460 specific polynucleotides. Of particular interest for identification of MON87460 polynucleotides is the use of PCR to amplify genomic DNA comprising transgene/genomic junction sequences.

Figure 2:
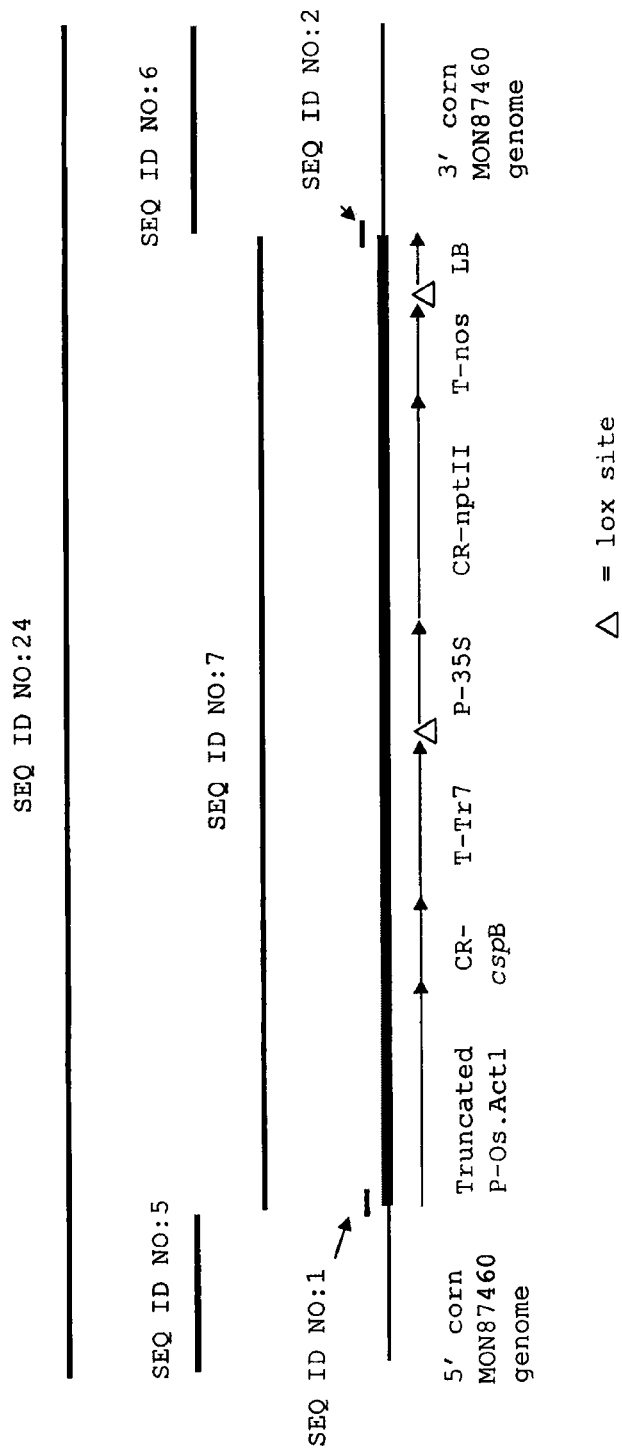
FIG. 2 illustrates the genomic organization of the transgene insert in corn plant MON87460.

An amplicon diagnostic for MON87460 comprises at least one junction sequence, SEQ ID NO: 1 or SEQ ID NO: 2 (FIG. 2). SEQ ID NO: 1 corresponds to the junction of the arbitrarily designated 5' flanking sequence (positions 1051 through 1060 of SEQ ID NO: 5) and the 5' region of the truncated rice actin promoter (positions 1-10 of SEQ ID NO:7) in the cspB expression construct. SEQ ID NO: 2 corresponds to the junction of the integrated left border from pMON73608 (positions 3300 through 3309 of SEQ ID NO: 7) and the arbitrarily designated 3' flanking sequence (positions 1 through 10 of SEQ ID NO: 6).

Event primer pairs that will produce a diagnostic amplicon for MON87460 include primer pairs based upon the flanking sequences and the inserted DNA from pMON73608. To generate a diagnostic amplicon comprising at least 11 nucleotides of SEQ ID NO: 1, a forward primer based upon SEQ ID NO: 5 and a reverse primer based upon the inserted transgene sequence, SEQ ID NO: 7 are prepared. Similarly, to generate a diagnostic amplicon comprising at least 11 nucleotides of SEQ ID NO: 2, a forward primer based upon inserted transgene sequence, SEQ ID NO: 7, and a reverse primer based upon the 3' flanking sequence, SEQ ID NO: 6 are prepared. It is readily apparent to one skilled in the art the primer pairs may also be designed to produce an amplicon comprising polynucleotides complementary to at least 11 nucleotides of SEQ ID NO:1 or SEQ ID NO:2, in which case the forward and reverse sequences are based upon sequences complementary to those in SEQ ID NO:5, SEQ ID NO:6, and SEQ ID NO:7.

Primers are designed which produce amplicons having between 50 and 1000 bases. Amplification conditions are as illustrated in Table 4 and Table 5 below and include a positive tissue control from event MON87460, a negative control from a corn plant that is not event MON87460, and a negative control that contains no corn genomic DNA. A primer pair that will amplify an endogenous corn DNA molecule, such as from the ADH gene, may be used as an internal control for the DNA amplification conditions.

Corn plant DNA for use in DNA amplification reactions may be isolated from any suitable corn plant tissue, and is preferably isolated from newly formed leaf tissue from plants <1 month old for reactions as described herein. Leaf tissue is harvested using a standard 7 mm hole punch, to collect tissue equivalent to an approximately 1 centimeter wide and 1 inch long leaf tear. Tissue samples are lyophilized and dried tissue is ground by adding 4-6 3 mm zirconia-silica beads to each tissue sample in a polypropylene tube and shaking in a paint shaker. Homogenized tissue samples are mixed in a 96-well plate with 395 ul of pre-warmed SDS extraction buffer (0.1M Tris pH 8, 10 mM EDTA, 1.0 M NaCl, 1% SDS), vortexed briefly and incubated at 65° C. for 45 minutes. 135 ul of cold potassium acetate (5M) is added. Samples are mixed by vortexing and the plate is spun at 3300 rpm for 20 minutes. 100 ul of supernatant is transferred to a fresh 96-well plate containing 100 ul isopropanol and samples are vortexed to mix. The plate is spun at 3300 rpm for 20 minutes and the supernatant discarded. Plates are drained upside down for 1 minute. 300 ul of cold 70% ethanol is added and the plate is vortexed briefly and placed at 4° C. for 30 minutes. The plate is spun at 3300 rpm for 20 minutes and supernatant is discarded. The plate is drained upside down and the ethanol precipitation repeated. After a final spin (3300 rpm 20 minutes), the plate is drained for one minute and placed on its side in a 65° C. oven for about 15-30 minutes to dry the pellet. The DNA is resuspended in 100 ul pH 8.0 TE buffer (Sigma) containing RNase (10 ug/ml. DNA is stored at 4° C. overnight. DNA yield is about 1 ug (long/ul).

The assay for the MON87460 amplicon can be performed using an Applied Biosystems GeneAmp PCR System 9700, Stratagene Robocycler, MJ Engine, Perkin-Elmer 9700 or Eppendorf Mastercycler Gradient thermocycler or any other amplification system that can be used to produce an amplicon diagnostic of MON87460.

TABLE 4

Corn MON87460 Event Specific PCR

| Step | Reagent | Volume | Comments |
|---|---|---|---|
| 1 | 18 megohm water | adjust for final volume of 10 ul | |
| 2 | 2X Universal Master Mix (Contains dNTPs, enzyme and buffer) | 5.0 ul | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer 1 at a concentration of 100 uM 100 ul of Primer 2 at a concentration of 100 uM 300 ul of 18 megohm water | 0.5 ul | 1.0 uM final concentration |
| 4 | Extracted DNA template (5-10 ng each): Leaf samples to be analyzed Negative control (non-transgenic DNA) Negative water control (no template control) Positive control (MON87460 DNA) | 3.0 ul | |

TABLE 5

Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute (−1° C./cycle) |

TABLE 5-continued

Endpoint TaqMan thermocycler conditions

| Cycle No. | Settings |
|---|---|
| 30 | 95° C. 15 seconds |
| | 54° C. 1 minute |
| 1 | 10° C. Forever |

Amplicons produced using the designed primer pairs are shown to contain MON87460 polynucleotides by hybridization to probes specific for MON87460 junction sequences SEQ ID NO:1 or SEQ ID NO:2, or by isolation and DNA sequence analysis.

Example 7 Endpoint TaqMan Event-Specific Assay

A MON87460 event-specific endpoint TaqMan PCR reaction is described herein. With Endpoint Taqman, the signal corresponding to a particular amplification is quantified using a fluorescent detection system after the reaction cycling is complete. The use of three site-specific hybridizations (two PCR primers and a fluorescently labeled probe) for signal generation provides a highly specific assay. The probe anneals to specific nucleotides between the forward and reverse primers. When nucleotide extension reaches the hybridized probe, taq polymerase degrades the probe releasing the fluor from the quencher so that a signal is emitted. The signal is read after the reactions are complete.

Polynucleotide primers used in the endpoint assay are primers SQ10443 (SEQ ID NO: 8), SQ10445 (SEQ ID NO: 9) and the probe used to detect the MON87460 amplicon is 6FAM™ labeled MGBNFQ (minor groove binding, non fluorescent quencher) probe PB3814 (SEQ ID NO: 10). An internal corn DNA primer may also be used to confirm integrity of the template DNA. For example, amplification of alcohol dehydrogenase (ADH), a single-copy endogenous gene within the corn genome, may be accomplished using primers SQ5263 (SEQ ID NO:11) and SQ5264 (SEQ ID NO:12) and detected with VIC™ (reporter fluorochrome) and TAMRA™ (quencher fluorochrome) probe PB2033 (SEQ ID NO:13). 6FAM™, VIC™ and TAMRA™ are fluorescent dye products of Applied Biosystems (Foster City, Calif.) attached to the DNA probes. In these analyses, Taq DNA polymerase cleaves probes that specifically hybridize to the amplified DNA and releases the fluorophore. The separation of fluorophore and quencher allows fluorescence to occur which is diagnostic under these conditions for the presence of MON87460 polynucleotides.

SQ10443 (SEQ ID NO: 8) and SQ10445 (SEQ ID NO: 9) when used as described in Table 2 below produce a 68 nt DNA amplicon (SEQ ID NO:20) that is diagnostic for event MON87460 DNA and detected by hybridization to a polynucleotide probe, such as PB3814. This assay has been optimized for use in 96-well or 384-well format using an Applied Biosystems GeneAmp PCR System 9700 or MJ Research DNA Engine PTC-225. Other methods and apparatus may be known to those skilled in the art and used to produce amplicons that identify the event MON87460 DNA. Adjustments to cycling parameters may be needed to ensure that ramp speeds are equivalent. Corn leaf tissue samples are used in the below analysis, and should be thoroughly ground to produce a homogenous sample. Corn leaf DNA is isolated as described in Example 6. The concentration of the leaf DNA to be tested is preferably within the range of 5-10 ng per PCR reaction. Control DNA should be extracted using the same method as for extraction of the samples to be analyzed. Controls for this analysis should include a positive control from corn known to contain event MON87460 DNA, a negative control from non-transgenic corn and a negative control that contains no template DNA.

For PCR reactions using an Applied Biosystems GeneAmp PCR System 9700 or MJ Research DNA Engine PTC-225 thermal cycler, cycling parameters as described in Table 3 below are used. When running the PCR in the Perkin-Elmer 9700, the thermocycler is run with the ramp speed set at maximum.

TABLE 7

Endpoint TaqMan thermocycler conditions

| Cycle No. | Settings |
| --- | --- |
| 1 | 50° C. 2 minutes |
| 1 | 95° C. 10 minutes |
| 10 | 95° C. 15 seconds |
|  | 64° C. 1 minute (−1° C./cycle) |
| 30 | 95° C. 15 seconds |
|  | 54° C. 1 minute |
| 1 | 10° C. Forever |

Example 8 Endpoint TaqMan PCR Zygosity Assay

A specific assay is described to detect the presence and zygosity (homozygous or hemiozygous) of MON87460 transgenic event in genomic DNA extracted from corn leaf tissue as described in Example 6. Determining zygosity for event MON87460 in a sample was done using an event-specific zygosity endpoint TaqMan PCR for which examples of conditions are described in Table 8 and Table 9. The DNA primers and probes used in the zygosity assay are primers SQ21105 (SEQ ID NO: 14) and SQ21106 (SEQ ID NO: 15), and 6FAM' labeled MGB (minor groove binding) probe PB3771 (SEQ ID NO:16) for detection of MON87460 junction polynucleotides, and primers SQ21195 (SEQ ID NO:17 and SQ21196 (SEQ ID NO:18), and VIC™ labeled MGB probe PB10223 (SEQ ID NO:19) for detection of wild-type corn DNA at the insertion site.

SQ21105 (SEQ ID NO: 14) and SQ21106 (SEQ ID NO: 15) when used in these reaction methods with PB3771 (SEQ ID NO:16) produce a 134 nt labeled DNA amplicon (SEQ ID NO:21) that is diagnostic for event MON87460 DNA.

TABLE 6

Corn MON87460 Event Specific Endpoint TaqMan PCR

| Step | Reagent | Volume | Comments |
| --- | --- | --- | --- |
| 1 | 18 megohm water | adjust for final volume of 10 ul |  |
| 2 | 2X Universal Master Mix (Contains dNTPs, enzyme and buffer) | 5.0 ul | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer SQ10443 at a concentration of 100 uM 100 ul of Primer SQ10445 at a concentration of 100 uM 300 ul of 18 megohm water | 0.5 ul | 1.0 uM final concentration |
| 4 | Event 6-FAM ™ MGBNFQ Probe PB3814 (resuspended in 18 megohm water to a concentration of 10 uM) | 0.2 ul | 0.2 uM final concentration |
| 5 | Internal Control Primer-1 (SQ5263) and Internal Control Primer-2 (SQ5264). Mix (resuspended in 18 megohm water to a concentration of 20 μM for each primer) | 0.5 μl | 1.0 μM final concentration |
| 6 | Internal Control VIC ™ Probe (PB2033; SEQ ID NO: 13) resuspended in 18 megohm water to a concentration of 10 μM | 0.2 μl | 0.2 μM final concentration |
| 7 | Extracted DNA template (5-10 ng each): Leaf samples to be analyzed Negative control (non-transgenic DNA) Negative water control (no template control) Positive control (MON87460 DNA) | 3.0 ul |  |

SQ21195 (SEQ ID NO:17 and SQ21196 (SEQ ID NO:18), when used in these reaction methods with PB2512 (SEQ ID NO: 12) produce a 145 nt DNA amplicon (SEQ ID NO:22) that is diagnostic for the wild type allele. The probe for this reaction is specific to the 22 bp deletion of genomic DNA (SEQ ID NO:23) that occurred at the MON87460 insertion site. Heterozygosity is determined by the presence of both amplicons as demonstrated by the liberation of fluorescent signal from both probes PB3771 and PB10223. Homozygous corn plant genetic material is identified by liberation of only the 6FAM' signal from PB3771. Controls for this analysis should include a positive control from corn plant samples homozygous and hemizygous for event MON87460 DNA, a negative control from non-transgenic corn, and a negative control that contains no template DNA.

This assay has been optimized for use in 96-well or 384-well format using an Applied Biosystems GeneAmp PCR System 9700 or MJ Research DNA Engine PTC-225. When running the PCR in the MJ Engine, the thermocycler should be run in the calculated mode. When running the PCR in the Perkin-Elmer 9700, the thermocycler is run with the ramp speed set at maximum.

TABLE 8

Corn MON87460 Event-Specific Zygosity Endpoint TaqMan PCR

| Step | Reagent | Volume | Comments |
|---|---|---|---|
| 1 | 18 megohm water | adjust for final volume of 10 ul | |
| 2 | 2X Universal Master Mix (Contains dNTPs, enzyme and buffer) | 5.0 ul | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer SQ21105 at a concentration of 100 uM 100 ul of Primer SQ21106 at a concentration of 100 uM 300 ul of 18 megohm water | 0.5 ul | 1.0 uM final concentration |
| 4 | Event 6-FAM ™ MGB Probe PB3771 (resuspended in 18 megohm water to a concentration of 10 uM) | 0.2 ul | 0.2 uM final concentration |
| 5 | Wild-type Primer-1 (SQ21195) and Wild-type Primer-2 (SQ21196) Mix (resuspended in 18 megohm water to a concentration of 20 μM for each primer) | 0.5 μl | 1.0 μM final concentration |
| 6 | Wild-type VIC ™ MGB Probe (PB10223) resuspended in 18 megohm water to a concentration of 10 μM | 0.2 μl | 0.2 μM final concentration |
| 7 | Extracted DNA template (5-10 ng each): Leaf samples to be analyzed Negative control (non-transgenic DNA) Negative water control (no template control) Positive control (Homozygous MON87460 DNA) Positive control (Hemizygous MON87460 DNA) | 3.0 ul | |

TABLE 9

Zygosity Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute (−1° C./cycle) |

TABLE 9-continued

Zygosity Endpoint TaqMan thermocycler conditions

| Cycle No. | Settings |
|---|---|
| 30 | 95° C. 15 seconds |
| | 54° C. 1 minute |
| 1 | 10° C. Forever |

Example 9 MON87460 Yield Performance

Additional field trials were conducted with CspB expressing event, MON87460, to further investigate the ability of this event to provide tolerance to water-deficits during the late vegetative and reproductive developmental stages. These are very important stages from an agricultural perspective due to the sensitivity of the crop at these growth stages and the frequency with which a drought occurs during these developmental stages in the growing regions targeted.

Yield performance of MON87460 was evaluated in three elite hybrid genetic backgrounds at 5 replicated locations across central California and western Kansas where two distinct limiting-water treatments were applied. The late vegetative treatment was applied to the trials by reducing irrigation for a 14 day period during the late vegetative stage of development, immediately prior to flowering. The treatment reduced the relative growth rate during the treatment by approximately 50% of well-watered rates and similarly reduced the average end of season grain yield by 50%. A grain fill treatment was achieved by initiating the water-limiting conditions at a later stage, relative to the vegetative treatment, depleting the soil moisture profile on or around flowering and achieving maximal stress during the grain fill period. This treatment resulted in an approximate 25% reduction in plant heights and a 30-40% reduction in grain yield as a result of the stress imposition. Three hybrids expressing the CspB event were evaluated using 20 replications of data across 5 locations for each stress treatment window.

Each trial location was designed as a 3 factor group unbalanced block design, and planted with 4 replications per location. Within each replication, the genotypes were randomized as the $1^{st}$ factor, and events, and gene-positive vs. gene-negative plots were randomized as the $2^{nd}$, and $3^{rd}$ factors, respectively. The design placed the positive and negative entries for each selection in adjacent 2 row plots. Final population density reflected local planting practices and ranged from 65 to 76 plants per 2 row plot. Plots were 21 feet long and row spacing ranged from 30 to 40 inches wide, reflecting local planting practices.

Analysis of the yield data was performed using Version 9.1.3 of SAS/STAT software (SAS Institute Inc., 2003). Analysis of variance calculations were performed using the MIXED and GLIMMIX procedures. Outliers were identified individually at each location by calculating the deleted Studentized residuals with respect to the corresponding linear model for a single location, comparing those residuals to zero using t-tests at an experiment wise Type I error rate of 5% using Bonferroni-adjusted p-values, and removing the identified outliers. After two passes through the data, all remaining observations were included in the analyses. Yield was determined for each plot, and analyzed using a mixed model with fixed effects for constructs and events nested within constructs and random effects for locations, reps within locations, and the interaction of locations with constructs. These analyses were performed separately for each hybrid. Comparisons of event and construct averages to negative paired entries were made with t-tests applied to least-squares means. Yield stability was examined by comparing simple linear regression estimates derived from positive and negative events. In both cases, the regression model included the average yield of the event at a location as the response and the average yield of a commercial check pedigree at the same location as the predictor. Positive and negative entries were then compared by using their predicted yields from the regression model at various benchmark yields of the commercial check.

MON87460 corn plants exhibited improvements in end of season grain yield across the different hybrid entries and under both water stress regimes when compared to a conventional wild-type control of the same genetic background (Table 10). Yield benefits in these experiments ranged from 11% to as much at 21% across yield values that averaged 6.4 to 8.5 t/Ha. The transgenic CspB event consistently outyielded the non-transgenic controls by at least 0.5 t/Ha across 12 out of 15 reproductive stress treatments and 13 out of 15 vegetative stress treatments.

TABLE 10

MON87460 Yield Results From Managed Irrigation Water-deficit Conditions

| Stress class | Entries | Mean Yld Pos (t/Ha) | Mean Yld Check (t/Ha) | t/Ha difference | % difference |
|---|---|---|---|---|---|
| Vegetative | Hybrid 1 (positive) | 10.1 | 8.5 | 1.6 | 19 |
| Reproductive | Hybrid 1 (positive) | 9.0 | 7.7 | 1.3 | 16 |
| All Stress | Hybrid 1 (positive) | 9.1 | 7.9 | 1.1 | 14 |
| Vegetative | Hybrid 2 (positive) | 7.7 | 6.5 | 1.2 | 18 |
| Reproductive | Hybrid 2 (positive) | 8.1 | 6.8 | 1.3 | 19 |
| All Stress | Hybrid 2 (positive) | 7.7 | 6.4 | 1.3 | 21 |
| Vegetative | Hybrid 3 (positive) | 8.3 | 7.2 | 1.1 | 16 |
| Reproductive | Hybrid 3 (positive) | 8.9 | 8.0 | 0.9 | 11 |
| All Stress | Hybrid 3 (positive) | 8.8 | 7.9 | 0.9 | 12 |

A multi-year analysis was also conducted with MON87460 to assess the stability of the yield advantages across locations under water-limiting conditions. Locations that had experienced some level of water stress, where yield reductions ranged from 20 to 80%, were compiled and analyzed. Yield advantages were evident across multiple years of testing and under a wide range of environments with varying degrees of water-deficit stress.

Across four years of testing, MON87460 has demonstrated an average yield benefit of 10.5% across three hybrid test-crosses under managed stress environmental testing. The average yield advantage each year was 0.89, 0.48, 0.49 and 0.79 t/Ha, representing percentage increases of 13.4, 6.7, 10.5 and 11.3%, respectively.

Dryland market evaluations of MON87460 hybrid entries were conducted in the states of South Dakota, Nebraska, and Kansas. Locations were selected on the basis of historical weather patterns and average county yields of 4.5 to 7.7 t/Ha. Each trial location was designed as a split-plot unbalanced block design and planted with a single replication per location. Plots were 100 feet long and four rows wide and final population densities reflected local planting practices under non-irrigated conditions of approximately 200 plants per 100 foot row. Row spacing ranged from 30 to 40 inches wide, reflecting local planting practices. Weather stations were installed at each location and the trials were monitored for signs of water-deficit stress throughout the season. No supplemental water was provided. Environmental data was collected and seasonal weather patterns, including rainfall accumulation, were utilized to classify the water-deficit stress during the season for each dryland location. 12 of the locations planted across these three states were categorized as having experienced water stress during the late vegetative through reproductive developmental stages and were utilized for analysis.

Yield benefits were observed in the same three hybrid backgrounds that were evaluated under controlled water-deficit conditions described in Table 10. When compared to the non-transgenic control, the MON87460 event provides yield benefits of up to 0.75 t/Ha, or 15%. These dryland growing conditions created a lower yielding environment (average yield of the controls were 4.9 t/Ha) than the controlled water-deficit locations where the overall yields of the controls ranged from 6.4 to 8.5 t/Ha.

Thus, significant yield improvements are obtained with MON87460 under controlled drought environments as well as under water stressed western dryland conditions. MON87460 provides water stress tolerance by using water more efficiently than negative controls by delivering improved growth rates and grain yields under water stress conditions while using equivalent or less water.

Example 10 Plant Breeding to Produce Herbicide Tolerant MON87460 Plants

MON87460 event plants are crossed with a herbicide tolerant corn plant expressing a glyphosate resistant 5-enol-pyruvylshikimate-3-phosphate synthase (EPSPS) gene to generate improved plants having both water deficit tolerance and herbicide tolerance. Of particular interest is a cross of a MON87460 event corn plant to a herbicide tolerant corn event plant designated as event PV-ZMGT32(nk603) and described in U.S. Pat. No. 6,825,400.

Crossing is conducted with two homozygous inbred lines, one of MON87460 and one of PV-ZMGT32(nk603) to produce hybrid seed for commercial planting of a corn crop having water deficit and herbicide tolerance.

Alternatively, a single inbred line comprising both MON87460 and PV-ZMGT32(nk603) is generated using a recurrent parent backcrossing breeding method to produce a fixed line homozygous for both traits. The inbred line developed in this manner exhibits water deficit tolerance and herbicide tolerance traits. The inbred line is crossed with a second inbred line, which may be an elite wild type line or a transgenic event line demonstrating one or more improved traits, to produce hybrid seed for planting to produce an improved corn crop.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A corn chromosome comprising SEQ ID NO:1 and a heterologous transgenic insert comprising a truncated rice actin promoter that is operably linked to a cspB gene.

2. The corn chromosome of claim 1, wherein a 5' terminus of said insert overlaps a 3' terminus of SEQ ID NO:1.

3. The corn chromosome of claim 1, wherein said corn chromosome further comprises SEQ ID NO:2.

4. The corn chromosome of claim 2, wherein said corn chromosome comprises SEQ ID NO:7 or SEQ ID NO:24.

5. A method of producing a drought tolerant corn plant, the method comprising crossing a drought tolerant first parent corn plant comprising a SEQ ID NO:1 and a heterologous transgenic insert comprising a truncated rice actin promoter that is operably linked to a cspB gene, and a second parent corn plant, thereby producing a plurality of drought tolerant progeny plants.

6. The method of claim 5, wherein said first and second corn plants are inbred plants and wherein hybrid corn seed is produced.

7. The method of claim 5, wherein said insert comprises SEQ ID NO:7 or SEQ ID NO:24.

8. A method for obtaining a water deficit tolerant corn plant that lacks an intact selectable marker gene comprising the steps of:

exposing a corn chromosome comprising SEQ ID NO:1 and a heterologous transgene insert to one or more recombination-inducing agents, wherein said heterologous transgene insert comprises a truncated rice actin promoter that is operably linked to a cspB gene, and a selectable marker gene;

selecting a corn plant comprising SEQ ID NO:1 and a truncated rice actin promoter that is operably linked to a cspB gene wherein said selectable marker gene or a portion thereof has been eliminated or disrupted, thereby obtaining a water deficit tolerant corn plant that lacks an intact selectable marker gene.

9. The method of claim 8, wherein said recombination-inducing agent comprises a recombinase, a nuclease, a homologous replacement sequence, a non-homologous replacement sequence, or a combination thereof.

10. The method of claim 9, wherein said homologous replacement sequence or said non-homologous replacement sequence comprises one or more genes.

11. The method of claim 8, wherein said heterologous transgene insert comprises SEQ ID NO: 7 or SEQ ID NO: 24.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial sequence
<220> FEATURE:
<223> OTHER INFORMATION: 5'junction sequence

<400> SEQUENCE: 1
ggctgtcttt gaggaggatc                                                   20

<210> SEQ ID NO 2
<211> LENGTH: 20
<212> TYPE: DNA
<213> ORGANISM: Artificial sequence
<220> FEATURE:
<223> OTHER INFORMATION: 3' junction sequence

<400> SEQUENCE: 2
tgtagatttc acgttgaaga                                                   20

<210> SEQ ID NO 3
<211> LENGTH: 30
<212> TYPE: DNA
<213> ORGANISM: Artificial sequence
<220> FEATURE:
<223> OTHER INFORMATION: 5'junction sequence

<400> SEQUENCE: 3
tagacggctg tctttgagga ggatcgcgag                                        30

<210> SEQ ID NO 4
<211> LENGTH: 30
<212> TYPE: DNA
<213> ORGANISM: Artificial sequence
<220> FEATURE:
<223> OTHER INFORMATION: 3' junction sequence

<400> SEQUENCE: 4
atccatgtag atttcacgtt gaagaaaaat                                        30
```

<210> SEQ ID NO 5
<211> LENGTH: 1060
<212> TYPE: DNA
<213> ORGANISM: Zea mays

<400> SEQUENCE: 5

```
gaggtcctgt atggaatcgt gttcgtttat ttcccggggg ccggggcaaa aaagacggca      60
atggattgtt ggacttgaca tgtgcggtgc gtgggtccaa cccggcctgg cttttgggcc     120
agcgcgggcc gacatagtga ggcccaaaat ttaaaaagca cagctgcagg cccacggaac     180
cagtggttat gaaaaacgga aacaaagata gtaaatttta cctccttaaa ttgccaccgt     240
atccaatatc caaattcagg taatctattc ctataaagca ccaatttccg ctcttttcat     300
ctatcgtctg tcatgcgctc tgttcctctc catcgtgtat cgcagataaa aggttacatg     360
catttccatg catgtgatgg gataaaaaca agaaaaaagg ttgacatgca tttccatgca     420
gataaaaggt tacatggatt tccttggaga agtataata agactaaatg ctgaggcgga     480
ggagagagag agaggagatg tgggtagtaa acttttagtc atctttgaca caagatcaaa     540
gaagatttgt gaaattatgc attaaaatat cgaagagcta actactacac gaataagcta     600
aatggtaggc tgcaaaggtg attacagcta gcagttgact ctattattaa acttcctctt     660
agggcaacag tagttggaaa ggttttttg gtgctgccca gatgcaaact aaaatccatg     720
catcctctct caacctggaa ggtgggccta aaaaagatga tctaccatcc acggatccac     780
ctgtcagctc aagttattgg gtttaggaaa cagggaccta cgtggagatg tgtgctggac     840
gggcgggcct cccacctgtc acgccgcagg cggaacggtg cgaaacgacg cacgcttttg     900
ctgtgcgcct gtgcgtctgg cggtcagcgc gagcgtgact gcgttttcgt ttgcgttaga     960
cgacgatcat cgctggaaat ttggtattct ctcacgttga aggaaaatgg attggaggga    1020
gtatgtagat aaattttcaa agcgttagac ggctgtcttt                          1060
```

<210> SEQ ID NO 6
<211> LENGTH: 1260
<212> TYPE: DNA
<213> ORGANISM: Zea mays

<400> SEQUENCE: 6

```
acgttgaaga aaaatggatg gagggaggaa gtagataaag ttttttgttg tatattgtga      60
ttttaatttg aaatcaagct tggtcaaacc gtggccgaaa tttggcctgg ccactaatgg     120
ccatgaacca agcgtagttt gccgattacc ccgtcccgac ggtacgactt tctctaatcg     180
ctcggttact gtccctgcaa cctgcatctc atgactccag gccggcccaa caccagcagc     240
gaccgcgacc aggctcctcc tcctcctcca gccacgggca agaggccgcg cgcatgctct     300
cgctcctgtt cccggtaatc cggcccagta ccttggtacc gcaccgtacc tgtaatctct     360
atctctagtt ctctagtaca tattaagtca atagtgtaga ctgtaacact accatgactt     420
catcctccct tacctcgctc tctgcgcacg cacaaaccac ccttccgccc catataggag     480
ccgatatcgt gcccccgtc ctggccgcac gcttccctaa cccctcgtgg actaggcttc     540
ccctccacga cgaggccacg acaatggttg ccccgcacg acgaggccgc ggtgtgggcg     600
aaggaggcga cgtgacctac agtccaaggc ctcacatcca catacatgcg tcatctaatt     660
gattaatcta tagcctggtc gcgctgtgct gctactgctt gatcgacgag tgctgttgcg     720
acccgtctgt catcttcgtc agctagacga agcatccgag tacaactcta aacatacgaa     780
catttaata acgagagcat ataacgataa atagtgcttc tacattaatg tatgttatca     840
```

| | | |
|---|---|---|
| atacttattg actcagtgac aaagcacgga catacatcta gtagttaata ataaaaataa | 900 |
| ataattacct tattaaacga tcatttatta tataaatgta tttattttt atgtacatat | 960 |
| aataagttat tacaatctga caatatatat aagtgataga acataaagta gaggaacaaa | 1020 |
| cggaacgtaa aggaaaacga agctagtcag gtagatgctc ccgaggacaa aaaaaaggg | 1080 |
| gcatagttgt caagtttaat cttcccaagt tttatcttac gtagtagtag agcgagagcg | 1140 |
| gtccaattaa gggcacgcac agttgcagca ggtgcagggc tccagtagcc gcggcgggta | 1200 |
| cgctcgcagt cgcagggcgc cgcgcctagt tctgctgccc ggcccgggtc atgaaccaac | 1260 |

<210> SEQ ID NO 7
<211> LENGTH: 3309
<212> TYPE: DNA
<213> ORGANISM: Artificial sequence
<220> FEATURE:
<223> OTHER INFORMATION: Inserted transgene cassette

<400> SEQUENCE: 7

| | | |
|---|---|---|
| gaggaggatc gcgagccagc gacgaggccg gccctccctc cgcttccaaa gaaacgcccc | 60 |
| ccatcgccac tatatacata cccccccctc tcctcccatc cccccaaccc taccaccacc | 120 |
| accaccacca cctccacctc ctcccccctc gctgccggac gacgagctcc tccccctcc | 180 |
| ccctccgccg ccgccgcgcc ggtaaccacc ccgcccctct cctctttctt tctccgtttt | 240 |
| ttttttccgt ctcggtctcg atctttggcc ttggtagttt gggtgggcga gaggcggctt | 300 |
| cgtgcgcgcc cagatcggtg cgcgggaggg gcgggatctc gcggctgggg ctctcgccgg | 360 |
| cgtggatccg gcccggatct cgcggggaat ggggctctcg gatgtagatc tgcgatccgc | 420 |
| cgttgttggg ggagatgatg gggggtttaa aatttccgcc atgctaaaca agatcaggaa | 480 |
| gaggggaaaa gggcactatg gtttatattt ttatatattt ctgctgcttc gtcaggctta | 540 |
| gatgtgctag atctttcttt cttcttttg tgggtagaat ttgaatccct cagcattgtt | 600 |
| catcggtagt ttttcttttc atgatttgtg acaaatgcag cctcgtgcgg agcttttttg | 660 |
| taggtagacc atggtagaag gtaaagtaaa atggttcaac tctgaaaaag gtttcggatt | 720 |
| catcgaagta gaaggtcaag acgatgtatt cgttcatttc tctgctattc aaggcgaagg | 780 |
| cttcaaaact ttagaagaag gccaagctgt ttcttttgaa atcgttgaag gaaaccgcgg | 840 |
| accacaagct gctaacgtta ctaaagaagc gtgaatttaa atgggcccgg gggatccact | 900 |
| agttctagct atatcatcaa tttatgtatt acacataata tcgcactcag tctttcatct | 960 |
| acggcaatgt accagctgat ataatcagtt attgaaatat ttctgaattt aaacttgcat | 1020 |
| caataaattt atgttttgc ttggactata atacctgact tgttatttta tcaataaata | 1080 |
| tttaaactat atttctttca agatatcatt ctttacaagt atacgtgttt aaattgaata | 1140 |
| ccataaattt ttatttttca aatacatgta aaattatgaa atgggagtgg tggcgaccga | 1200 |
| gctcaagcac acttcaattc ctataacgga ccaaatcgca aaaattataa taacatatta | 1260 |
| tttcatcctg gattaaaaga aagtcaccgg ggattatttt gtgacgccga ttacatacgg | 1320 |
| cgacaataaa gacattggaa atcgtagtac atattggaat acactgatta tattaatgat | 1380 |
| gaatacatac tttaatatcc ttacgtagga tcgatccgaa ttcgcgacac gcggccgctc | 1440 |
| tagaactagt ggatccccc cttaattaag ggggctgcag gaattcataa cttcgtataa | 1500 |
| tgtatgctat acgaagttat agcttggtcg agtggaagct agctttccga tcctacctgt | 1560 |
| cacttcatca aaaggacagt agaaaaggaa ggtggcacct acaaatgcca tcattgcgat | 1620 |

-continued

```
aaaggaaagg ctatcattca agatgcctct gccgacagtg gtcccaaaga tggaccccca    1680
cccacgagga gcatcgtgga aaaagaagac gttccaacca cgtcttcaaa gcaagtggat    1740
tgatgtgata cttccactga cgtaagggat gacgcacaat cccactatcc ttcgcaagac    1800
ccttcctcta tataaggaag ttcatttcat ttggagagga cacgctgaaa tcaccagtct    1860
ctctctacaa gatcggggat ctctagctag acgatcgttt cgcatgattg aacaagatgg    1920
attgcacgca ggttctccgg ccgcttgggt ggagaggcta ttcggctatg actgggcaca    1980
acagacaatc ggctgctctg atgccgccgt gttccggctg tcagcgcagg ggcgcccggt    2040
tcttttgtc aagaccgacc tgtccggtgc cctgaatgaa ctgcaggacg aggcagcgcg    2100
gctatcgtgg ctggccacga cgggcgttcc ttgcgcagct gtgctcgacg ttgtcactga    2160
agcgggaagg gactggctgc tattgggcga agtgccgggg caggatctcc tgtcatctca    2220
ccttgctcct gccgagaaag tatccatcat ggctgatgca atgcggcggc tgcatacgct    2280
tgatccggct acctgcccat tcgaccacca agcgaaacat cgcatcgagc gagcacgtac    2340
tcggatggaa gccggtcttg tcgatcagga tgatctggac gaagagcatc aggggctcgc    2400
gccagccgaa ctgttcgcca ggctcaaggc gcgcatgccc gacggcgagg atctcgtcgt    2460
gacccatggc gatgcctgct tgccgaatat catggtggaa aatggccgct ttctggatt    2520
catcgactgt ggccggctgg gtgtggcgga ccgctatcag gacatagcgt tggctacccg    2580
tgatattgct gaagagcttg gcggcgaatg ggctgaccgc ttcctcgtgc tttacggtat    2640
cgccgctccc gattcgcagc gcatcgcctt ctatcgcctt cttgacgagt tcttctgagc    2700
gggactctgg ggttcgatcc ccaattcccg atcgttcaaa catttggcaa taaagtttct    2760
taagattgaa tcctgttgcc ggtcttgcga tgattatcat ataatttctg ttgaattacg    2820
ttaagcatgt aataattaac atgtaatgca tgacgttatt tatgagatgg gtttttatga    2880
ttagagtccc gcaattatac atttaatacg cgatagaaaa caaaatatag cgcgcaaact    2940
aggataaatt atcgcgcgcg gtgtcatcta tgttactaga tcggggatcg ggccactcga    3000
ccaagctata acttcgtata atgtatgcta tacgaagtta tcgcgccaaa tcgtgaagtt    3060
tctcatctaa gccccatttt ggacgtgaat gtagacacgt cgaaataaag atttccgaat    3120
tagaataatt tgtttattgc tttcgcctat aaatacgacg gatcgtaatt tgtcgtttta    3180
tcaaaatgta ctttcatttt ataataacgc tgcggacatc tacattttg aattgaaaaa    3240
aaattggtaa ttactctttc tttttctcca tattgaccat catactcatt gctgatccat    3300
gtagatttc                                                           3309
```

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
ttgaccatca tactcattgc tg                                              22

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9 cttcctcccct ccatccattt t                                           21

<210> SEQ ID NO 10
<211> LENGTH: 21
<212> TYPE: DNA
<213> ORGANISM: Artificial sequence
<220> FEATURE:
<223> OTHER INFORMATION: Probe

<400> SEQUENCE: 10
tcttcaacgt gaaatctaca t                                            21

<210> SEQ ID NO 11
<211> LENGTH: 18
<212> TYPE: DNA
<213> ORGANISM: Artificial sequence
<220> FEATURE:
<223> OTHER INFORMATION: Primer

<400> SEQUENCE: 11
ccagcctcat ggccaaag                                                18

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ccttcttggc ggcttatctg                                              20

<210> SEQ ID NO 13
<211> LENGTH: 26
<212> TYPE: DNA
<213> ORGANISM: Artificial sequence
<220> FEATURE:
<223> OTHER INFORMATION: Probe

<400> SEQUENCE: 13
cttaggggca gactcccgtg ttccct                                       26

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
ggtttgacca agcttgattt caa                                          23

<210> SEQ ID NO 15
<211> LENGTH: 27
<212> TYPE: DNA
<213> ORGANISM: Artificial sequence
<220> FEATURE:
<223> OTHER INFORMATION: Primer

<400> SEQUENCE: 15
ctccatattg accatcatac tcattgc                                      27

<210> SEQ ID NO 16
<211> LENGTH: 24
<212> TYPE: DNA

<210> SEQ ID NO 16
<211> LENGTH: 24
<212> TYPE: DNA
<213> ORGANISM: Artificial sequence
<220> FEATURE:
<223> OTHER INFORMATION: Probe

<400> SEQUENCE: 16
tgatccatgt agatttcacg ttga                                          24

<210> SEQ ID NO 17
<211> LENGTH: 23
<212> TYPE: DNA
<213> ORGANISM: Artificial sequence
<220> FEATURE:
<223> OTHER INFORMATION: Primer

<400> SEQUENCE: 17
tcaaagcgtt agacggctgt ctt                                           23

<210> SEQ ID NO 18
<211> LENGTH: 18
<212> TYPE: DNA
<213> ORGANISM: Artificial sequence
<220> FEATURE:
<223> OTHER INFORMATION: Primer

<400> SEQUENCE: 18
ttcggccacg gtttgacc                                                 18

<210> SEQ ID NO 19
<211> LENGTH: 20
<212> TYPE: DNA
<213> ORGANISM: Artificial sequence
<220> FEATURE:
<223> OTHER INFORMATION: Probe

<400> SEQUENCE: 19
tgctggaaat ttggtattct                                               20

<210> SEQ ID NO 20
<211> LENGTH: 68
<212> TYPE: DNA
<213> ORGANISM: Artificial sequence
<220> FEATURE:
<223> OTHER INFORMATION: Amplicon

<400> SEQUENCE: 20
ttgaccatca tactcattgc tgatccatgt agatttcacg ttgaagaaaa atggatggag   60
ggaggaag                                                            68

<210> SEQ ID NO 21
<211> LENGTH: 134
<212> TYPE: DNA
<213> ORGANISM: Artificial sequence
<220> FEATURE:
<223> OTHER INFORMATION: Amplicon

<400> SEQUENCE: 21
ctccatattg accatcatac tcattgctga tccatgtaga tttcacgttg aagaaaaatg   60
gatggaggga ggaagtagat aaagtttttt gttgtatatt gtgattttaa tttgaaatca  120
agcttggtca aacc                                                    134

<210> SEQ ID NO 22
<211> LENGTH: 145
<212> TYPE: DNA
<213> ORGANISM: Zea mays

```
<220> FEATURE:
<223> OTHER INFORMATION: Amplicon

<400> SEQUENCE: 22
tcaaagcgtt agacggctgt ctttgctgga aatttggtat tctctcacgt tgaagaaaaa      60
tggatggagg gaggaagtag ataaagtttt ttgttgtata ttgtgatttt aatttgaaat     120
caagcttggt caaaccgtgg ccgaa                                          145

<210> SEQ ID NO 23
<211> LENGTH: 22
<212> TYPE: DNA
<213> ORGANISM: Zea mays

<400> SEQUENCE: 23
gctggaaatt tggtattctc tc                                              22

<210> SEQ ID NO 24
<211> LENGTH: 5629
<212> TYPE: DNA
<213> ORGANISM: Artificial sequence
<220> FEATURE:
<223> OTHER INFORMATION: Transgene and corn genome sequence at junction

<400> SEQUENCE: 24
gaggtcctgt atggaatcgt gttcgtttat ttcccggggg ccggggcaaa aaagacggca      60
atggattgtt ggacttgaca tgtgcggtgc gtgggtccaa cccggcctgg cttttgggcc     120
agcgcgggcc gacatagtga ggcccaaaat ttaaaaagca cagctgcagg cccacggaac     180
cagtggttat gaaaaacgga aacaaagata gtaaatttta cctccttaaa ttgccaccgt     240
atccaatatc caaattcagg taatctattc ctataaagca ccaatttccg ctcttttcat     300
ctatcgtctg tcatgcgctc tgttcctctc catcgtgtat cgcagataaa aggttacatg     360
catttccatg catgtgatgg gataaaaaca agaaaaaagg ttgacatgca tttccatgca     420
gataaaaggt tacatggatt tccttggaga agtataata agactaaatg ctgaggcgga     480
ggagagagag agaggagatg tgggtagtaa acttttagtc atctttgaca caagatcaaa     540
gaagatttgt gaaattatgc attaaaatat cgaagagcta actactacac gaataagcta     600
aatggtaggc tgcaaaggtg attacagcta gcagttgact ctattattaa acttcctctt     660
agggcaacag tagttggaaa ggttttttg gtgctgccca gatgcaaact aaaatccatg     720
catcctctct caacctggaa ggtgggccta aaaagatga tctaccatcc acggatccac     780
ctgtcagctc aagttattgg gtttaggaaa cagggaccta cgtggagatg tgtgctggac     840
gggcgggcct cccacctgtc acgccgcagg cggaacggtg cgaaacgacg cacgcttttg     900
ctgtgcgcct gtgcgtctgg cggtcagcgc gagcgtgact gcgttttcgt ttgcgttaga     960
cgacgatcat cgctggaaat ttggtattct ctcacgttga aggaaaatgg attggaggga    1020
gtatgtagat aaattttcaa agcgttagac ggctgtcttt gaggaggatc gcagccagc     1080 gacgaggccg gccctccctc gcttccaaa gaaacgcccc catcgccac tatatacata     1140 ccccccccctc tcctcccatc cccccaaccc taccaccacc accaccacca cctccacctc    1200 ctccccccctc gctgccggac gacgagctcc tcccccctcc cctccgccg ccgccgcgcc    1260 ggtaaccacc ccgcccctct cctctttctt tctccgtttt ttttttccgt ctcggtctcg    1320
atctttggcc ttggtagttt gggtgggcga gaggcggctt cgtgcgcgcc cagatcggtg    1380
cgcgggaggg gcgggatctc gcggctgggg ctctcgccgg cgtggatccg gcccggatct    1440
```

```
cgcggggaat ggggctctcg gatgtagatc tgcgatccgc cgttgttggg ggagatgatg    1500
gggggtttaa aatttccgcc atgctaaaca agatcaggaa gaggggaaaa gggcactatg    1560
gtttatattt ttatatattt ctgctgcttc gtcaggctta gatgtgctag atctttcttt    1620 cttcttttg tgggtagaat ttgaatccct cagcattgtt catcggtagt ttttcttttc    1680
atgatttgtg acaaatgcag cctcgtgcgg agcttttttg taggtagacc atggtagaag    1740
gtaaagtaaa atggttcaac tctgaaaaag gtttcggatt catcgaagta aaggtcaag    1800 acgatgtatt cgttcatttc tctgctattc aaggcgaagg cttcaaaact ttagaagaag    1860
gccaagctgt ttcttttgaa atcgttgaag gaaaccgcgg accacaagct gctaacgtta    1920
ctaaagaagc gtgaatttaa atgggcccgg gggatccact agttctagct atatcatcaa    1980
tttatgtatt acacataata tcgcactcag tctttcatct acggcaatgt accagctgat    2040
ataatcagtt attgaaatat ttctgaattt aaacttgcat caataaattt atgttttgc    2100 ttggactata atacctgact tgttatttta tcaataaata tttaaactat atttctttca    2160
agatatcatt ctttacaagt atacgtgttt aaattgaata ccataaattt ttattttca    2220 aatacatgta aaattatgaa atgggagtgg tggcgaccga gctcaagcac acttcaattc    2280
ctataacgga ccaaatcgca aaaattataa taacatatta tttcatcctg gattaaaga    2340 aagtcaccgg ggattatttt gtgacgccga ttacatacgg cgacaataaa gacattggaa    2400
atcgtagtac atattggaat acactgatta tattaatgat gaatacatac tttaatatcc    2460
ttacgtagga tcgatccgaa ttcgcgacac gcggccgctc tagaactagt ggatccccc    2520 cttaattaag gggctgcag gaattcataa cttcgtataa tgtatgctat acgaagttat    2580
agcttggtcg agtggaagct agcttttccga tcctacctgt cacttcatca aaaggacagt    2640 agaaaggaa ggtggcacct acaaatgcca tcattgcgat aaaggaaagg ctatcattca    2700
agatgcctct gccgacagtg gtcccaaaga tggacccca cccacgagga gcatcgtgga    2760
aaaagaagac gttccaacca cgtcttcaaa gcaagtggat tgatgtgata cttccactga    2820
cgtaagggat gacgcacaat cccactatcc ttcgcaagac ccttcctcta tataaggaag    2880
ttcatttcat ttggagagga cacgctgaaa tcaccagtct ctctctacaa gatcggggat    2940
ctctagctag acgatcgttt cgcatgattg aacaagatgg attgcacgca ggttctccgg    3000
ccgcttgggt ggagaggcta ttcggctatg actgggcaca acagacaatc ggctgctctg    3060
atgccgccgt gttccggctg tcagcgcagg ggcgcccggt tctttttgtc aagaccgacc    3120
tgtccggtgc cctgaatgaa ctgcaggacg aggcagcgcg gctatcgtgg ctggccacga    3180
cgggcgttcc ttgcgcagct gtgctcgacg ttgtcactga agcgggaagg gactggctgc    3240
tattgggcga agtgccgggg caggatctcc tgtcatctca ccttgctcct gccgagaaag    3300
tatccatcat ggctgatgca atgcggcggc tgcatacgct tgatccggct acctgcccat    3360
tcgaccacca agcgaaacat cgcatcgagc gagcacgtac tcggatggaa gccggtcttg    3420
tcgatcagga tgatctggac gaagagcatc agggctcgc gccagccgaa ctgttcgcca    3480
ggctcaaggc gcgcatgccc gacggcgagg atctcgtcgt gacgcatggc gatgcctgct    3540
tgccgaatat catggtggaa aatggccgct ttctggatt catcgactgt ggccggctgg    3600
gtgtggcgga ccgctatcag gacatagcgt tggctaccc tgatattgct gaagagcttg    3660
gcggcgaatg ggctgaccgc ttcctcgtgc tttacggtat cgccgctccc gattcgcagc    3720
gcatcgcctt ctatcgcctt cttgacgagt tcttctgagc gggactctgg ggttcgatcc    3780
ccaattcccg atcgttcaaa catttggcaa taaagtttct taagattgaa tcctgttgcc    3840
```

-continued

```
ggtcttgcga tgattatcat ataatttctg ttgaattacg ttaagcatgt aataattaac    3900
atgtaatgca tgacgttatt tatgagatgg gtttttatga ttagagtccc gcaattatac    3960
atttaatacg cgatagaaaa caaaatatag cgcgcaaact aggataaatt atcgcgcgcg    4020
gtgtcatcta tgttactaga tcggggatcg ggccactcga ccaagctata acttcgtata    4080
atgtatgcta tacgaagtta tcgcgccaaa tcgtgaagtt tctcatctaa gcccccattt    4140
ggacgtgaat gtagacacgt cgaaataaag atttccgaat tagaataatt tgtttattgc    4200
tttcgcctat aaatacgacg gatcgtaatt tgtcgtttta tcaaaatgta ctttcatttt    4260
ataataacgc tgcggacatc tacatttttg aattgaaaaa aaattggtaa ttactctttc    4320
tttttctcca tattgaccat catactcatt gctgatccat gtagatttca cgttgaagaa    4380
aaatggatgg agggaggaag tagataaagt tttttgttgt atattgtgat tttaatttga    4440
aatcaagctt ggtcaaaccg tggccgaaat ttggcctggc cactaatggc catgaaccaa    4500
gcgtagtttg ccgattaccc cgtcccgacg gtacgacttt ctctaatcgc tcggttactg    4560
tccctgcaac ctgcatctca tgactccagg ccggcccaac accagcagcg accgcgacca    4620
ggctcctcct cctcctccag ccacgggcaa gaggccgcgc gcatgctctc gctcctgttc    4680
ccggtaatcc ggcccagtac cttggtaccg caccgtacct gtaatctcta tctctagttc    4740
tctagtacat attaagtcaa tagtgtagac tgtaacacta ccatgacttc atcctccctt    4800
acctcgctct ctgcgcacgc acaaaccacc cttccgcccc atataggagc cgatatcgtg    4860 cccccccgtcc tggccgcacg cttccctaac ccctcgtgga ctaggcttcc cctccacgac    4920
gaggccacga caatggttgc ccccgcacga cgaggccgcg gtgtgggcga aggaggcgac    4980
gtgacctaca gtccaaggcc tcacatccac atacatgcgt catctaattg attaatctat    5040
agcctggtcg cgctgtgctg ctactgcttg atcgacgagt gctgttgcga cccgtctgtc    5100
atcttcgtca gctagacgaa gcatccgagt acaactctaa acatacgaac atttttaataa    5160 cgagagcata taacgataaa tagtgcttct acattaatgt atgttatcaa tacttattga    5220
ctcagtgaca aagcacggac atacatctag tagttaataa taaaaataaa taattacctt    5280
attaaacgat catttattat ataaatgtat ttatttttta tgtacatata ataagttatt    5340
acaatctgac aatatatata agtgatagaa cataaagtag aggaacaaac ggaacgtaaa    5400
ggaaaacgaa gctagtcagg tagatgctcc cgaggacaaa aaaaaggggg catagttgtc    5460
aagtttaatc ttcccaagtt ttatcttacg tagtagtaga gcgagagcgg tccaattaag    5520
ggcacgcaca gttgcagcag gtgcagggct ccagtagccg cggcgggtac gctcgcagtc    5580
gcagggcgcc gcgcctagtt ctgctgcccg gcccgggtca tgaaccaac             5629
```

<210> SEQ ID NO 25
<211> LENGTH: 22
<212> TYPE: DNA
<213> ORGANISM: Artificial sequence
<220> FEATURE:
<223> OTHER INFORMATION: 5' junction

<400> SEQUENCE: 25

```
cggctgtctt tgaggaggat cg                                             22
```